United States Patent
Habeck et al.

[11] Patent Number: 5,945,091
[45] Date of Patent: Aug. 31, 1999

[54] PHOTO-STABLE COSMETIC AND PHARMACEUTICAL FORMULATIONS CONTAINING UV-FILTERS

[75] Inventors: Thorsten Habeck, Meckenheim; Alexander Aumüller, Neustadt; Volker Schehlmann, Römerberg; Horst Westenfelder, Neustadt; Thomas Wünsch, Speyer, all of Germany

[73] Assignee: BASF Aktiengesellschaft, Ludwigshafen, Germany

[21] Appl. No.: 08/972,391

[22] Filed: Nov. 18, 1997

[30] Foreign Application Priority Data

Nov. 29, 1996 [DE] Germany ............... 196 49 381
Mar. 21, 1997 [DE] Germany ............... 197 12 033

[51] Int. Cl.⁶ ............... A61K 7/42; A61K 7/00; A61K 31/66; A61K 31/255; A61K 31/275
[52] U.S. Cl. ............... 424/59; 424/60; 424/400; 424/401; 514/114; 514/119; 514/517; 514/519; 514/526; 514/528; 514/541; 514/616; 514/627; 514/666
[58] Field of Search ............... 424/59, 60, 400, 424/401; 514/114, 119, 517, 519, 526, 528, 541, 616, 627, 666

[56] References Cited

U.S. PATENT DOCUMENTS

| | | | |
|---|---|---|---|
| 5,629,007 | 5/1997 | Audia et al. | 424/423 |
| 5,637,718 | 6/1997 | Bird et al. | 546/315 |
| 5,670,514 | 9/1997 | Audia et al. | 514/298 |
| 5,830,441 | 11/1998 | Wang et al. | 424/59 |

*Primary Examiner*—Shelley A. Dodson
*Attorney, Agent, or Firm*—Keil & Weinkauf

[57] ABSTRACT

A method of using compounds of formula I

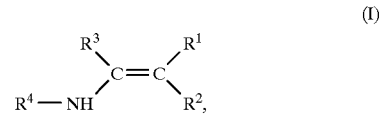

in which the C=C double bond is present in E and/or Z configuration and the variables have the following meanings:

$R^1$ denotes $COOR^5$, $COR^5$, $CONR^5R^6$, $CN$, $O=S(-R^5)=O$, $O=S(-OR^5)=O$, $R^7O-P(-OR^8)=O$;

$R^2$ denotes $COOR^6$, $COR^6$, $CONR^5R^6$, $CN$, $O=S(-R^6)=O$, $O=S(-OR^6)=O$, $R^7O-P(-OR^8)=O$;

$R^3$ denotes hydrogen, an optionally substituted aliphatic, cycloaliphatic, araliphatic or aromatic radical having in each case up to 18 carbon atoms;

$R^4$ denotes an optionally substituted aromatic or heteroaromatic radical containing from 5 to 12 ring atoms;

$R^5$ to $R^8$ independently denote hydrogen, an open-chain or branched-chain aliphatic, araliphatic, cycloaliphatic or optionally substituted aromatic radical containing in each case up to 18 carbon atoms, where the variables $R^3$ to $R^8$ may also form, together with the carbon atoms to which they are attached, a 5-membered or 6-membered ring, which may be anellated if desired, as UV filters, particularly UV-A filters, in cosmetic and pharmaceutical formulations for the protection of the human skin or human hair from solar radiation, alone or together with compounds known per se in cosmetic and pharmaceutical formulations and capable of absorbing radiation in the UV range.

11 Claims, No Drawings

PHOTO-STABLE COSMETIC AND PHARMACEUTICAL FORMULATIONS CONTAINING UV-FILTERS

The invention relates to the use of enamine derivatives as photo-stable UV filters in cosmetic and pharmaceutical formulations for the protection of the human epidermis or human hair from UV radiation, specifically that ranging from 320 to 400 nm.

It is the purpose of the screening agents used in cosmetic and pharmaceutical formulations to prevent injurious influences of sunlight on the human skin or at least to reduce the effects thereof. On the other hand these screening agents also serve to protect other ingredients from destruction or degradation due to UV radiation. In hair-care formulations it is desirable to reduce damage to the keratin fiber caused by UV radiation.

The sunlight reaching the earth's surface has a concentration of UV-B radiation (from 280 to 320 nm) and UV-A radiation (>320 nm), which follow directly on the visible light range. The effect thereof on the human skin is demonstrated by sunburn, this being particularly so in the case of UV-B radiation. Accordingly the market offers a relatively large number of substances which absorb UV-B radiation and thus prevent sunburn.

Dermatological investigations have now shown that UV-A radiation can also cause skin lesions and allergies by, for example, causing damage to keratin or elastin. This means that the elasticity and water-holding capacity of the skin are reduced, ie the skin is less supple and tends to form wrinkles. The remarkably high abundance of skin cancer in areas of strong sunshine clearly shows that damage to hereditary factors in the cells is caused by sunlight, specifically by UV-A radiation. Knowing all this, it is clear that the development of efficient filtering substances for the UV-A range is necessary.

There is a growing need for screening agents for cosmetic and pharmaceutical formulations which may primarily serve as UV-A filters and whose absorption maxima should therefore be in the range of from approximately 320 to 380 nm. In order to achieve the desired action with a minimal amount of material, such screening agents should additionally show a high degree of specific absorption.

Furthermore, screening agents for cosmetic preparations must also satisfy a large number of other demands, for example show good solubility in cosmetic oils, high stability of the emulsions prepared therefrom, toxicological acceptability and also little intrinsic odor and little intrinsic color.

Another requirement to be satisfied by screening agents is: adequate photostability. However, this is not or only insufficiently provided by the hitherto available screening agents for the absorption of UV-A radiation.

In French patent specification No. 2,440,933, 4-(1,1-dimethylethyl)-4-methoxy-dibenzoylmethane is described as a UV-A filter. It is proposed therein that this specific UV-A filter, which is sold by GIVAUDAN under the trade name "PARSOL 1789", be used in combination with UV-B filters in order to absorb all of the UV radiation having a wavelength from 280 to 380 nm.

However, this UV-A filter, when used alone or in combination with UV-B filters, is not sufficiently photochemically stable to ensure constant protection of the skin during a lengthy sunbath, which makes it necessary to re-apply it to the skin at regular short intervals, if it is desired to achieve effective protection of the skin from the entire range of UV radiation.

EP 0,514,491 therefore proposes that the insufficiently photo-stable UV-A filters be stabilized by the addition of 2-cyano-3,3-diphenylacrylates, which are themselves active as filters for the UV-B range.

Furthermore, EP 251,398 has already proposed that chromophores that are capable of absorbing UV-A radiation and UV-B radiation be combined to a single molecule by a connecting link. This suffers from the drawbacks that free combination of UV-A filters and UV-B filters in cosmetic formulations is no longer possible and that difficulties encountered in chemically linking the chromophores permit the use of only certain combinations.

It is thus an object of the present invention to propose screening agents for cosmetic and pharmaceutical purposes which achieve high absorption in the UV-A range and which are photo-stable, have little intrinsic color ie exhibit a well-defined band structure and are soluble in oil or water depending on the substituent incorporated.

This object is achieved, according to the invention, by the use of compounds of Formula I

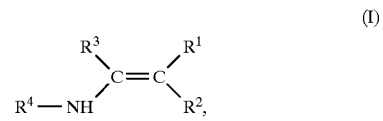

(I)

in which the C=C double bond is present in E and/or Z configuration and the variables have the following meanings:

$R^1$ denotes $COOR^5$, $COR^5$, $CONR^5R^6$, $CN$, $O=S(-R^5)=O$, $O=S(-OR^5)=O$, $R^7O-P(-OR^8)=O$;

$R^2$ denotes $COOR^6$, $COR^6$, $CONR^5R^6$, $CN$, $O=S(-R^6)=O$, $O=S(-OR^6)=O$, $R^7O-P(-OR^8)=O$;

$R^3$ denotes hydrogen, an optionally substituted aliphatic, cycloaliphatic, araliphatic or aromatic radical having in each case up to 18 carbon atoms;

$R^4$ denotes an optionally substituted aromatic or heteroaromatic radical containing from 5 to 12 ring atoms;

$R^5$ to $R^8$ independently denote hydrogen, an open-chain or branched-chain aliphatic, araliphatic, cycloaliphatic or optionally substituted aromatic radical containing in each case up to 18 carbon atoms, where the variables $R^3$ to $R^8$ may also form, together with the carbon atoms to which they are attached, a 5-membered or 6-membered ring, which may be anellated if desired, as UV filters, particularly UV-A filters, in cosmetic and pharmaceutical formulations for the protection of the human skin or human hair from solar radiation, alone or together with compounds known per se in cosmetic and pharmaceutical formulations and capable of absorbing radiation in the UV range.

We prefer those compounds of formula I, in which $R^3$ stands for hydrogen, $R^1$ for $CN$, $COOR^5$ and $COR^5$ and $R^2$ for $CN$, $COOR^6$ and $COR^6$, where $R^5$ and $R^6$ independently denote open-chain or branched-chain aliphatic or optionally substituted aromatic radicals containing up to 8 carbon atoms.

We particularly prefer the use of compounds of formula I in which $R^3$ stands for hydrogen, $R^1$ for $CN$, $COOR^5$ and $COR^5$ and $R^2$ for $CN$, $COOR^6$ and $COR^6$, where $R^5$ and $R^6$ independently denote open-chain or branched-chain aliphatic or optionally substituted aromatic radicals containing up to 8 carbon atoms and $R^4$ stands for an optionally substituted aromatic or heteroaromatic radical containing up to 10 carbon atoms in the ring, particularly a substituted phenyl, thienyl, furyl, pyridyl, indolyl or naphthylene radical and more preferably stands for an optionally substituted phenyl or thienyl radical.

Suitable substituents comprise both lipophilic and hydrophilic substituents containing, eg up to 20 carbon atoms. Lipophilic radicals, ie radicals which improve the oil-solubility is solubility of the compounds of formula I are, for example, aliphatic or cycloaliphatic radicals, particularly alkyl radicals containing from 1 to 18 carbon atoms, alkoxy, monoalkylamino and dialkylamino, alkoxycarbonyl, monoalkyl- and dialkyl-amino-carbonyl, monoalkyl- and dialkyl-aminosulfonyl radicals, and also cyanogeno, nitro, bromo, chloro, iodo or fluoro substituents.

Hydrophilic radicals, ie radicals which make the compounds of formula I soluble in water, are, for example, carboxy and sulfoxy radicals and particularly their salts with any physiologically acceptable cation, such as the alkali metal salts or the trialkylammonium salts, such as tri(hydroxyalkyl)ammonium salts or 2-methyl-propan-1-ol-2-ammonium salts. Other suitable radicals are ammonium, particularly alkylammonium, radicals containing any physiologically acceptable anion.

Suitable alkoxy radicals are those containing from 1 to 12 carbon atoms, preferably those having from 1 to 8 carbon atoms.

Specific examples thereof are:

| | |
|---|---|
| methoxy | ethoxy |
| isopropoxy | n-propoxy |
| 1-methlypropoxy | n-butoxy |
| n-pentoxy | 2-methylpropoxy |
| 3-methylbutoxy | 1,1-dimethylpropoxy |
| 2,2-dimethylpropoxy | hexoxy |
| 1-methyl-1-ethylpropoxy | heptoxy |
| octoxy | 2-ethylhexoxy |

Suitable monoalkylamino or dialkylamino radicals are for example those containing alkyl radicals having from 1 to 8 carbon atoms, such as methyl, n-propyl, n-butyl, 2-methylpropyl, 1,1-dimethylpropyl, hexyl, heptyl, 2-ethylhexyl, isopropyl, 1-methylpropyl, n-pentyl, 3-methylbutyl, 2,2-dimethylpropyl, 1-methyl-1-ethylpropyl and octyl. These radicals are also present in the monoalkyl- and dialkylaminocarbonyl radicals and the corresponding sulfonyl radicals.

Alkoxycarbonyl radicals are eg esters which contain the aforementioned alkoxy radicals or radicals of higher alcohols, eg, those containing up to 20 carbon atoms, such as iso-$C_{15}$-alcohol.

The invention also relates to the novel compounds of formula II,

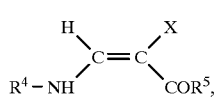

(II)

in which the C=C double bond is present in E and/or Z configuration and in which X denotes a cyanogen radical or $COCH_3$, $R^4$ denotes a phenyl radical which, when X is CN, may be substituted by one or more alkyl, alkoxy, alkylaminocarbonyl or alkoxycarbonyl radicals, containing in each case up to 20 carbon atoms, or cyanogen or carboxy radicals, and also by water-soluble substituents selected from the group consisting of carboxylate, sulfonate or ammonium radicals, for example alkali metal carboxylate or carbonyloxytri(hydroxyethyl)ammonium or sulfonyloxytri(hydroxyethyl)ammonium radicals, or, when X is $COCH_3$, may be substituted by one or more alkoxy radicals containing up to 20 carbon atoms or alkoxycarbonyl radicals containing 4 to 20 carbon atoms, and also by water-soluble substituents selected from the group consisting of carboxylate, sulfonate or ammonium radicals, and $R^5$, when X is CN, denotes a $C(CH_3)_3$ radical or, when X is $COCH_3$, an open-chain, branched-chain or cyclic alkyl, alkoxy, or alkoxyalkyl group containing in each case up to 18 carbon atoms, or an aryloxy group.

Table 1 below lists the preferred compounds of formula II of the invention.

TABLE 1

$X = COCH3$

| Y | $R^5$ | n | Position |
|---|---|---|---|
| $C_3H_7OCO$ | $CH_3$ | 1 | para |
| $C_3H_7OCO$ | $CH_3$ | 1 | meta |
| $C_3H_7OCO$ | $CH_3$ | 1 | ortho |
| $C_3H_7OCO$ | $CH_3$ | 2 | ortho/para |
| $C_4H_9OCO$ | $CH_3$ | 1 | para |
| $C_4H_9OCO$ | $CH_3$ | 1 | meta |
| $C_4H_9OCO$ | $CH_3$ | 1 | ortho |
| $C_4H_9OCO$ | $CH_3$ | 2 | ortho/para |
| $C_5H_{11}OCO$ | $CH_3$ | 1 | para |
| $C_5H_{11}OCO$ | $CH_3$ | 1 | meta |
| $C_5H_{11}OCO$ | $CH_3$ | 1 | ortho |
| $C_5H_{11}OCO$ | $CH_3$ | 2 | ortho/para |
| $C_6H_{13}OCO$ | $CH_3$ | 1 | para |
| $C_6H_{13}OCO$ | $CH_3$ | 1 | meta |
| $C_6H_{13}OCO$ | $CH_3$ | 1 | ortho |
| $C_6H_{13}OCO$ | $CH_3$ | 2 | ortho/para |
| $C_8H_{17}OCO$ | $CH_3$ | 1 | para |
| $C_8H_{17}OCO$ | $CH_3$ | 1 | meta |
| $C_8H_{17}OCO$ | $CH_3$ | 1 | ortho |
| $C_8H_{17}OCO$ | $CH_3$ | 2 | ortho/para |
| $C_{12}H_{25}OCO$ | $CH_3$ | 1 | para |
| $C_{12}H_{25}OCO$ | $CH_3$ | 1 | meta |
| $C_{12}H_{25}OCO$ | $CH_3$ | 1 | ortho |
| $C_{12}H_{25}OCO$ | $CH_3$ | 2 | ortho/para |
| $C_{13}H_{27}OCO$ | $CH_3$ | 1 | para |
| $C_{13}H_{27}OCO$ | $CH_3$ | 1 | meta |
| $C_{13}H_{27}OCO$ | $CH_3$ | 1 | ortho |
| $C_{13}H_{27}OCO$ | $CH_3$ | 2 | ortho/para |
| $C_{14}H_{29}OCO$ | $CH_3$ | 1 | para |
| $C_{14}H_{29}OCO$ | $CH_3$ | 1 | meta |
| $C_{14}H_{29}OCO$ | $CH_3$ | 1 | ortho |
| $C_{14}H_{29}OCO$ | $CH_3$ | 2 | ortho/para |
| $C_{15}H_{31}OCO$ | $CH_3$ | 1 | para |
| $C_{15}H_{31}OCO$ | $CH_3$ | 1 | meta |
| $C_{15}H_{31}OCO$ | $CH_3$ | 1 | ortho |
| $C_{15}H_{31}OCO$ | $CH_3$ | 2 | ortho/para |
| $C_{16}H_{33}OCO$ | $CH_3$ | 1 | para |
| $C_{16}H_{33}OCO$ | $CH_3$ | 1 | meta |
| $C_{16}H_{33}OCO$ | $CH_3$ | 1 | ortho |
| $C_{16}H_{33}OCO$ | $CH_3$ | 2 | ortho/para |
| $C_{17}H_{35}OCO$ | $CH_3$ | 1 | para |
| $C_{17}H_{35}OCO$ | $CH_3$ | 1 | meta |
| $C_{17}H_{35}OCO$ | $CH_3$ | 1 | ortho |
| $C_{17}H_{35}OCO$ | $CH_3$ | 2 | ortho/para |
| $C_{18}H_{37}OCO$ | $CH_3$ | 1 | para |
| $C_{18}H_{37}OCO$ | $CH_3$ | 1 | meta |
| $C_{18}H_{37}OCO$ | $CH_3$ | 1 | ortho |
| $C_{18}H_{37}OCO$ | $CH_3$ | 2 | ortho/para |
| $C_3H_7OCO$ | $C_2H_5$ | 1 | para |
| $C_3H_7OCO$ | $C_2H_5$ | 1 | meta |
| $C_3H_7OCO$ | $C_2H_5$ | 1 | ortho |
| $C_3H_7OCO$ | $C_2H_5$ | 2 | ortho/para |
| $C_4H_9OCO$ | $C_2H_5$ | 1 | para |
| $C_4H_9OCO$ | $C_2H_5$ | 1 | meta |
| $C_4H_9OCO$ | $C_2H_5$ | 1 | ortho |
| $C_4H_9OCO$ | $C_2H_5$ | 2 | ortho/para |

TABLE 1-continued

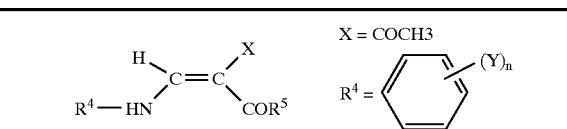

X = COCH3

| Y | R⁵ | n | Position |
|---|---|---|---|
| $C_5H_{11}OCO$ | $C_2H_5$ | 1 | para |
| $C_5H_{11}OCO$ | $C_2H_5$ | 1 | meta |
| $C_5H_{11}OCO$ | $C_2H_5$ | 1 | ortho |
| $C_5H_{11}OCO$ | $C_2H_5$ | 2 | ortho/para |
| $C_6H_{13}OCO$ | $C_2H_5$ | 1 | para |
| $C_6H_{13}OCO$ | $C_2H_5$ | 1 | meta |
| $C_6H_{13}OCO$ | $C_2H_5$ | 1 | ortho |
| $C_6H_{13}OCO$ | $C_2H_5$ | 2 | ortho/para |
| $C_8H_{17}OCO$ | $C_2H_5$ | 1 | para |
| $C_8H_{17}OCO$ | $C_2H_5$ | 1 | meta |
| $C_8H_{17}OCO$ | $C_2H_5$ | 1 | ortho |
| $C_8H_{17}OCO$ | $C_2H_5$ | 2 | ortho/para |
| $C_{12}H_{25}OCO$ | $C_2H_5$ | 1 | para |
| $C_{12}H_{25}OCO$ | $C_2H_5$ | 1 | meta |
| $C_{12}H_{25}OCO$ | $C_2H_5$ | 1 | ortho |
| $C_{12}H_{25}OCO$ | $C_2H_5$ | 2 | ortho/para |
| $C_{13}H_{27}OCO$ | $C_2H_5$ | 1 | para |
| $C_{13}H_{27}OCO$ | $C_2H_5$ | 1 | meta |
| $C_{13}H_{27}OCO$ | $C_2H_5$ | 1 | ortho |
| $C_{13}H_{27}OCO$ | $C_2H_5$ | 2 | ortho/para |
| $C_{14}H_{29}OCO$ | $C_2H_5$ | 1 | para |
| $C_{14}H_{29}OCO$ | $C_2H_5$ | 1 | meta |
| $C_{14}H_{29}OCO$ | $C_2H_5$ | 1 | ortho |
| $C_{14}H_{29}OCO$ | $C_2H_5$ | 2 | ortho/para |
| $C_{15}H_{31}OCO$ | $C_2H_5$ | 1 | para |
| $C_{15}H_{31}OCO$ | $C_2H_5$ | 1 | meta |
| $C_{15}H_{31}OCO$ | $C_2H_5$ | 1 | ortho |
| $C_{15}H_{31}OCO$ | $C_2H_5$ | 2 | ortho/para |
| $C_{16}H_{33}OCO$ | $C_2H_5$ | 1 | para |
| $C_{16}H_{33}OCO$ | $C_2H_5$ | 1 | meta |
| $C_{16}H_{33}OCO$ | $C_2H_5$ | 1 | ortho |
| $C_{16}H_{33}OCO$ | $C_2H_5$ | 2 | ortho/para |
| $C_{17}H_{35}OCO$ | $C_2H_5$ | 1 | para |
| $C_{17}H_{35}OCO$ | $C_2H_5$ | 1 | meta |
| $C_{17}H_{35}OCO$ | $C_2H_5$ | 1 | ortho |
| $C_{17}H_{35}OCO$ | $C_2H_5$ | 2 | ortho/para |
| $C_{18}H_{37}OCO$ | $C_2H_5$ | 1 | para |
| $C_{18}H_{37}OCO$ | $C_2H_5$ | 1 | meta |
| $C_{18}H_{37}OCO$ | $C_2H_5$ | 1 | ortho |
| $C_{18}H_{37}OCO$ | $C_2H_5$ | 2 | ortho/para |
| $C_3H_7OCO$ | $C_3H_7$ | 1 | para |
| $C_3H_7OCO$ | $C_3H_7$ | 1 | meta |
| $C_3H_7OCO$ | $C_3H_7$ | 1 | ortho |
| $C_3H_7OCO$ | $C_3H_7$ | 2 | ortho/para |
| $C_4H_9OCO$ | $C_3H_7$ | 1 | para |
| $C_4H_9OCO$ | $C_3H_7$ | 1 | meta |
| $C_4H_9OCO$ | $C_3H_7$ | 1 | ortho |
| $C_4H_9OCO$ | $C_3H_7$ | 2 | ortho/para |
| $C_5H_{11}OCO$ | $C_3H_7$ | 1 | para |
| $C_5H_{11}OCO$ | $C_3H_7$ | 1 | meta |
| $C_5H_{11}OCO$ | $C_3H_7$ | 1 | ortho |
| $C_5H_{11}OCO$ | $C_3H_7$ | 2 | ortho/para |
| $C_6H_{13}OCO$ | $C_3H_7$ | 1 | para |
| $C_6H_{13}OCO$ | $C_3H_7$ | 1 | meta |
| $C_6H_{13}OCO$ | $C_3H_7$ | 1 | ortho |
| $C_6H_{13}OCO$ | $C_3H_7$ | 2 | ortho/para |
| $C_8H_{17}OCO$ | $C_3H_7$ | 1 | para |
| $C_8H_{17}OCO$ | $C_3H_7$ | 1 | meta |
| $C_8H_{17}OCO$ | $C_3H_7$ | 1 | ortho |
| $C_8H_{17}OCO$ | $C_3H_7$ | 2 | ortho/para |
| $C_{12}H_{25}OCO$ | $C_3H_7$ | 1 | para |
| $C_{12}H_{25}OCO$ | $C_3H_7$ | 1 | meta |
| $C_{12}H_{25}OCO$ | $C_3H_7$ | 1 | ortho |
| $C_{12}H_{25}OCO$ | $C_3H_7$ | 2 | ortho/para |
| $C_{13}H_{27}OCO$ | $C_3H_7$ | 1 | para |
| $C_{13}H_{27}OCO$ | $C_3H_7$ | 1 | meta |
| $C_{13}H_{27}OCO$ | $C_3H_7$ | 1 | ortho |
| $C_{13}H_{27}OCO$ | $C_3H_7$ | 2 | ortho/para |
| $C_{14}H_{29}OCO$ | $C_3H_7$ | 1 | para |
| $C_{14}H_{29}OCO$ | $C_3H_7$ | 1 | meta |

TABLE 1-continued

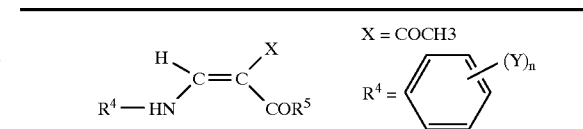

X = COCH3

| Y | R⁵ | n | Position |
|---|---|---|---|
| $C_{14}H_{29}OCO$ | $C_3H_7$ | 1 | ortho |
| $C_{14}H_{29}OCO$ | $C_3H_7$ | 2 | ortho/para |
| $C_{15}H_{31}OCO$ | $C_3H_7$ | 1 | para |
| $C_{15}H_{31}OCO$ | $C_3H_7$ | 1 | meta |
| $C_{15}H_{31}OCO$ | $C_3H_7$ | 1 | ortho |
| $C_{15}H_{31}OCO$ | $C_3H_7$ | 2 | ortho/para |
| $C_{16}H_{33}OCO$ | $C_3H_7$ | 1 | para |
| $C_{16}H_{33}OCO$ | $C_3H_7$ | 1 | meta |
| $C_{16}H_{33}OCO$ | $C_3H_7$ | 1 | ortho |
| $C_{16}H_{33}OCO$ | $C_3H_7$ | 2 | ortho/para |
| $C_{17}H_{35}OCO$ | $C_3H_7$ | 1 | para |
| $C_{17}H_{35}OCO$ | $C_3H_7$ | 1 | meta |
| $C_{17}H_{35}OCO$ | $C_3H_7$ | 1 | ortho |
| $C_{17}H_{35}OCO$ | $C_3H_7$ | 2 | ortho/para |
| $C_{18}H_{37}OCO$ | $C_3H_7$ | 1 | para |
| $C_{18}H_{37}OCO$ | $C_3H_7$ | 1 | meta |
| $C_{18}H_{37}OCO$ | $C_3H_7$ | 1 | ortho |
| $C_{18}H_{37}OCO$ | $C_3H_7$ | 2 | ortho/para |
| $C_3H_7OCO$ | $C_4H_9$ | 1 | para |
| $C_3H_7OCO$ | $C_4H_9$ | 1 | meta |
| $C_3H_7OCO$ | $C_4H_9$ | 1 | ortho |
| $C_3H_7OCO$ | $C_4H_9$ | 2 | ortho/para |
| $C_4H_9OCO$ | $C_4H_9$ | 1 | para |
| $C_4H_9OCO$ | $C_4H_9$ | 1 | meta |
| $C_4H_9OCO$ | $C_4H_9$ | 1 | ortho |
| $C_4H_9OCO$ | $C_4H_9$ | 2 | ortho/para |
| $C_5H_{11}OCO$ | $C_4H_9$ | 1 | para |
| $C_5H_{11}OCO$ | $C_4H_9$ | 1 | meta |
| $C_5H_{11}OCO$ | $C_4H_9$ | 1 | ortho |
| $C_5H_{11}OCO$ | $C_4H_9$ | 2 | ortho/para |
| $C_6H_{13}OCO$ | $C_4H_9$ | 1 | para |
| $C_6H_{13}OCO$ | $C_4H_9$ | 1 | meta |
| $C_6H_{13}OCO$ | $C_4H_9$ | 1 | ortho |
| $C_6H_{13}OCO$ | $C_4H_9$ | 2 | ortho/para |
| $C_8H_{17}OCO$ | $C_4H_9$ | 1 | para |
| $C_8H_{17}OCO$ | $C_4H_9$ | 1 | meta |
| $C_8H_{17}OCO$ | $C_4H_9$ | 1 | ortho |
| $C_8H_{17}OCO$ | $C_4H_9$ | 2 | ortho/para |
| $C_{12}H_{25}OCO$ | $C_4H_9$ | 1 | para |
| $C_{12}H_{25}OCO$ | $C_4H_9$ | 1 | meta |
| $C_{12}H_{25}OCO$ | $C_4H_9$ | 1 | ortho |
| $C_{12}H_{25}OCO$ | $C_4H_9$ | 2 | ortho/para |
| $C_{13}H_{27}OCO$ | $C_4H_9$ | 1 | para |
| $C_{13}H_{27}OCO$ | $C_4H_9$ | 1 | meta |
| $C_{13}H_{27}OCO$ | $C_4H_9$ | 1 | ortho |
| $C_{13}H_{27}OCO$ | $C_4H_9$ | 2 | ortho/para |
| $C_{14}H_{29}OCO$ | $C_4H_9$ | 1 | para |
| $C_{14}H_{29}OCO$ | $C_4H_9$ | 1 | meta |
| $C_{14}H_{29}OCO$ | $C_4H_9$ | 1 | ortho |
| $C_{14}H_{29}OCO$ | $C_4H_9$ | 2 | ortho/para |
| $C_{15}H_{31}OCO$ | $C_4H_9$ | 1 | para |
| $C_{15}H_{31}OCO$ | $C_4H_9$ | 1 | meta |
| $C_{15}H_{31}OCO$ | $C_4H_9$ | 1 | ortho |
| $C_{15}H_{31}OCO$ | $C_4H_9$ | 2 | ortho/para |
| $C_{16}H_{33}OCO$ | $C_4H_9$ | 1 | para |
| $C_{16}H_{33}OCO$ | $C_4H_9$ | 1 | meta |
| $C_{16}H_{33}OCO$ | $C_4H_9$ | 1 | ortho |
| $C_{16}H_{33}OCO$ | $C_4H_9$ | 2 | ortho/para |
| $C_{17}H_{35}OCO$ | $C_4H_9$ | 1 | para |
| $C_{17}H_{35}OCO$ | $C_4H_9$ | 1 | meta |
| $C_{17}H_{35}OCO$ | $C_4H_9$ | 1 | ortho |
| $C_{17}H_{35}OCO$ | $C_4H_9$ | 2 | ortho/para |
| $C_{18}H_{37}OCO$ | $C_4H_9$ | 1 | para |
| $C_{18}H_{37}OCO$ | $C_4H_9$ | 1 | meta |
| $C_{18}H_{37}OCO$ | $C_4H_9$ | 1 | ortho |
| $C_{18}H_{37}OCO$ | $C_4H_9$ | 2 | ortho/para |
| $C_3H_7OCO$ | $C_5H_{11}$ | 1 | para |
| $C_3H_7OCO$ | $C_5H_{11}$ | 1 | meta |
| $C_3H_7OCO$ | $C_5H_{11}$ | 1 | ortho |
| $C_3H_7OCO$ | $C_5H_{11}$ | 2 | ortho/para |

TABLE 1-continued

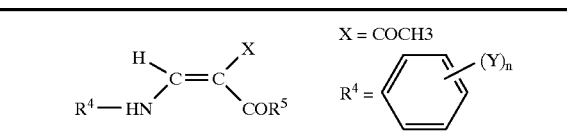

| Y | R⁵ | n | Position |
|---|----|---|----------|
| $C_4H_9OCO$ | $C_5H_{11}$ | 1 | para |
| $C_4H_9OCO$ | $C_5H_{11}$ | 1 | meta |
| $C_4H_9OCO$ | $C_5H_{11}$ | 1 | ortho |
| $C_4H_9OCO$ | $C_5H_{11}$ | 2 | ortho/para |
| $C_5H_{11}OCO$ | $C_5H_{11}$ | 1 | para |
| $C_5H_{11}OCO$ | $C_5H_{11}$ | 1 | meta |
| $C_5H_{11}OCO$ | $C_5H_{11}$ | 1 | ortho |
| $C_5H_{11}OCO$ | $C_5H_{11}$ | 2 | ortho/para |
| $C_6H_{13}OCO$ | $C_5H_{11}$ | 1 | para |
| $C_6H_{13}OCO$ | $C_5H_{11}$ | 1 | meta |
| $C_6H_{13}OCO$ | $C_5H_{11}$ | 1 | ortho |
| $C_6H_{13}OCO$ | $C_5H_{11}$ | 2 | ortho/para |
| $C_8H_{17}OCO$ | $C_5H_{11}$ | 1 | para |
| $C_8H_{17}OCO$ | $C_5H_{11}$ | 1 | meta |
| $C_8H_{17}OCO$ | $C_5H_{11}$ | 1 | ortho |
| $C_8H_{17}OCO$ | $C_5H_{11}$ | 2 | ortho/para |
| $C_{12}H_{25}OCO$ | $C_5H_{11}$ | 1 | para |
| $C_{12}H_{25}OCO$ | $C_5H_{11}$ | 1 | meta |
| $C_{12}H_{25}OCO$ | $C_5H_{11}$ | 1 | ortho |
| $C_{12}H_{25}OCO$ | $C_5H_{11}$ | 2 | ortho/para |
| $C_{13}H_{27}OCO$ | $C_5H_{11}$ | 1 | para |
| $C_{13}H_{27}OCO$ | $C_5H_{11}$ | 1 | meta |
| $C_{13}H_{27}OCO$ | $C_5H_{11}$ | 1 | ortho |
| $C_{13}H_{27}OCO$ | $C_5H_{11}$ | 2 | ortho/para |
| $C_{14}H_{29}OCO$ | $C_5H_{11}$ | 1 | para |
| $C_{14}H_{29}OCO$ | $C_5H_{11}$ | 1 | meta |
| $C_{14}H_{29}OCO$ | $C_5H_{11}$ | 1 | ortho |
| $C_{14}H_{29}OCO$ | $C_5H_{11}$ | 2 | ortho/para |
| $C_{15}H_{31}OCO$ | $C_5H_{11}$ | 1 | para |
| $C_{15}H_{31}OCO$ | $C_5H_{11}$ | 1 | meta |
| $C_{15}H_{31}OCO$ | $C_5H_{11}$ | 1 | ortho |
| $C_{15}H_{31}OCO$ | $C_5H_{11}$ | 2 | ortho/para |
| $C_{16}H_{33}OCO$ | $C_5H_{11}$ | 1 | para |
| $C_{16}H_{33}OCO$ | $C_5H_{11}$ | 1 | meta |
| $C_{16}H_{33}OCO$ | $C_5H_{11}$ | 1 | ortho |
| $C_{16}H_{33}OCO$ | $C_5H_{11}$ | 2 | ortho/para |
| $C_{17}H_{35}OCO$ | $C_5H_{11}$ | 1 | para |
| $C_{17}H_{35}OCO$ | $C_5H_{11}$ | 1 | para |
| $C_{17}H_{35}OCO$ | $C_5H_{11}$ | 1 | meta |
| $C_{17}H_{35}OCO$ | $C_5H_{11}$ | 1 | ortho |
| $C_{17}H_{35}OCO$ | $C_5H_{11}$ | 2 | ortho/para |
| $C_{18}H_{37}OCO$ | $C_5H_{11}$ | 1 | para |
| $C_{18}H_{37}OCO$ | $C_5H_{11}$ | 1 | meta |
| $C_{18}H_{37}OCO$ | $C_5H_{11}$ | 1 | ortho |
| $C_{18}H_{37}OCO$ | $C_5H_{11}$ | 2 | ortho/para |
| $C_3H_7OCO$ | $C_6H_{13}$ | 1 | para |
| $C_3H_7OCO$ | $C_6H_{13}$ | 1 | meta |
| $C_3H_7OCO$ | $C_6H_{13}$ | 1 | ortho |
| $C_3H_7OCO$ | $C_6H_{13}$ | 2 | ortho/para |
| $C_4H_9OCO$ | $C_6H_{13}$ | 1 | para |
| $C_4H_9OCO$ | $C_6H_{13}$ | 1 | meta |
| $C_4H_9OCO$ | $C_6H_{13}$ | 1 | ortho |
| $C_4H_9OCO$ | $C_6H_{13}$ | 2 | ortho/para |
| $C_5H_{11}OCO$ | $C_6H_{13}$ | 1 | para |
| $C_5H_{11}OCO$ | $C_6H_{13}$ | 1 | meta |
| $C_5H_{11}OCO$ | $C_6H_{13}$ | 1 | ortho |
| $C_5H_{11}OCO$ | $C_6H_{13}$ | 2 | ortho/para |
| $C_6H_{13}OCO$ | $C_6H_{13}$ | 1 | para |
| $C_6H_{13}OCO$ | $C_6H_{13}$ | 1 | meta |
| $C_6H_{13}OCO$ | $C_6H_{13}$ | 1 | ortho |
| $C_6H_{13}OCO$ | $C_6H_{13}$ | 2 | ortho/para |
| $C_8H_{17}OCO$ | $C_6H_{13}$ | 1 | para |
| $C_8H_{17}OCO$ | $C_6H_{13}$ | 1 | meta |
| $C_8H_{17}OCO$ | $C_6H_{13}$ | 1 | ortho |
| $C_8H_{17}OCO$ | $C_6H_{13}$ | 2 | ortho/para |
| $C_{12}H_{25}OCO$ | $C_6H_{13}$ | 1 | para |
| $C_{12}H_{25}OCO$ | $C_6H_{13}$ | 1 | meta |
| $C_{12}H_{25}OCO$ | $C_6H_{13}$ | 1 | ortho |
| $C_{12}H_{25}OCO$ | $C_6H_{13}$ | 2 | ortho/para |
| $C_{13}H_{27}OCO$ | $C_6H_{13}$ | 1 | para |

TABLE 1-continued

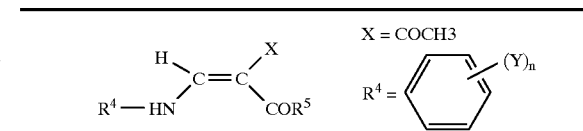

| Y | R⁵ | n | Position |
|---|----|---|----------|
| $C_{13}H_{27}OCO$ | $C_6H_{13}$ | 1 | meta |
| $C_{13}H_{27}OCO$ | $C_6H_{13}$ | 1 | ortho |
| $C_{13}H_{27}OCO$ | $C_6H_{13}$ | 2 | ortho/para |
| $C_{14}H_{29}OCO$ | $C_6H_{13}$ | 1 | para |
| $C_{14}H_{29}OCO$ | $C_6H_{13}$ | 1 | meta |
| $C_{14}H_{29}OCO$ | $C_6H_{13}$ | 1 | ortho |
| $C_{14}H_{29}OCO$ | $C_6H_{13}$ | 2 | ortho/para |
| $C_{15}H_{31}OCO$ | $C_6H_{13}$ | 1 | para |
| $C_{15}H_{31}OCO$ | $C_6H_{13}$ | 1 | meta |
| $C_{15}H_{31}OCO$ | $C_6H_{13}$ | 1 | ortho |
| $C_{15}H_{31}OCO$ | $C_6H_{13}$ | 2 | ortho/para |
| $C_{16}H_{33}OCO$ | $C_6H_{13}$ | 1 | para |
| $C_{16}H_{33}OCO$ | $C_6H_{13}$ | 1 | meta |
| $C_{16}H_{33}OCO$ | $C_6H_{13}$ | 1 | ortho |
| $C_{16}H_{33}OCO$ | $C_6H_{13}$ | 2 | ortho/para |
| $C_{17}H_{35}OCO$ | $C_6H_{13}$ | 1 | para |
| $C_{17}H_{35}OCO$ | $C_6H_{13}$ | 1 | meta |
| $C_{17}H_{35}OCO$ | $C_6H_{13}$ | 1 | ortho |
| $C_{17}H_{35}OCO$ | $C_6H_{13}$ | 2 | ortho/para |
| $C_{18}H_{37}OCO$ | $C_6H_{13}$ | 1 | para |
| $C_{18}H_{37}OCO$ | $C_6H_{13}$ | 1 | meta |
| $C_{18}H_{37}OCO$ | $C_6H_{13}$ | 1 | ortho |
| $C_{18}H_{37}OCO$ | $C_6H_{13}$ | 2 | ortho/para |
| $C_3H_7OCO$ | $CH_3O$ | 1 | para |
| $C_3H_7OCO$ | $CH_3O$ | 1 | meta |
| $C_3H_7OCO$ | $CH_3O$ | 1 | ortho |
| $C_3H_7OCO$ | $CH_3O$ | 2 | ortho/para |
| $C_4H_9OCO$ | $CH_3O$ | 1 | para |
| $C_4H_9OCO$ | $CH_3O$ | 1 | meta |
| $C_4H_9OCO$ | $CH_3O$ | 1 | ortho |
| $C_4H_9OCO$ | $CH_3O$ | 2 | ortho/para |
| $C_5H_{11}OCO$ | $CH_3O$ | 1 | para |
| $C_5H_{11}OCO$ | $CH_3O$ | 1 | meta |
| $C_5H_{11}OCO$ | $CH_3O$ | 1 | ortho |
| $C_5H_{11}OCO$ | $CH_3O$ | 2 | ortho/para |
| $C_6H_{13}OCO$ | $CH_3O$ | 1 | para |
| $C_6H_{13}OCO$ | $CH_3O$ | 1 | meta |
| $C_6H_{13}OCO$ | $CH_3O$ | 1 | ortho |
| $C_6H_{13}OCO$ | $CH_3O$ | 2 | ortho/para |
| $C_8H_{17}OCO$ | $CH_3O$ | 1 | para |
| $C_8H_{17}OCO$ | $CH_3O$ | 1 | meta |
| $C_8H_{17}OCO$ | $CH_3O$ | 1 | ortho |
| $C_8H_{17}OCO$ | $CH_3O$ | 2 | ortho/para |
| $C_{12}H_{25}OCO$ | $CH_3O$ | 1 | para |
| $C_{12}H_{25}OCO$ | $CH_3O$ | 1 | meta |
| $C_{12}H_{25}OCO$ | $CH_3O$ | 1 | ortho |
| $C_{12}H_{25}OCO$ | $CH_3O$ | 2 | ortho/para |
| $C_{13}H_{27}OCO$ | $CH_3O$ | 1 | para |
| $C_{13}H_{27}OCO$ | $CH_3O$ | 1 | meta |
| $C_{13}H_{27}OCO$ | $CH_3O$ | 1 | ortho |
| $C_{13}H_{27}OCO$ | $CH_3O$ | 2 | ortho/para |
| $C_{14}H_{29}OCO$ | $CH_3O$ | 1 | para |
| $C_{14}H_{29}OCO$ | $CH_3O$ | 1 | meta |
| $C_{14}H_{29}OCO$ | $CH_3O$ | 1 | ortho |
| $C_{14}H_{29}OCO$ | $CH_3O$ | 2 | ortho/para |
| $C_{15}H_{31}OCO$ | $CH_3O$ | 1 | para |
| $C_{15}H_{31}OCO$ | $CH_3O$ | 1 | meta |
| $C_{15}H_{31}OCO$ | $CH_3O$ | 1 | ortho |
| $C_{15}H_{31}OCO$ | $CH_3O$ | 2 | ortho/para |
| $C_{16}H_{33}OCO$ | $CH_3O$ | 1 | para |
| $C_{16}H_{33}OCO$ | $CH_3O$ | 1 | meta |
| $C_{16}H_{33}OCO$ | $CH_3O$ | 1 | ortho |
| $C_{16}H_{33}OCO$ | $CH_3O$ | 2 | ortho/para |
| $C_{17}H_{35}OCO$ | $CH_3O$ | 1 | para |
| $C_{17}H_{35}OCO$ | $CH_3O$ | 1 | meta |
| $C_{17}H_{35}OCO$ | $CH_3O$ | 1 | ortho |
| $C_{17}H_{35}OCO$ | $CH_3O$ | 2 | ortho/para |
| $C_{18}H_{37}OCO$ | $CH_3O$ | 1 | para |
| $C_{18}H_{37}OCO$ | $CH_3O$ | 1 | meta |
| $C_{18}H_{37}OCO$ | $CH_3O$ | 1 | ortho |

TABLE 1-continued

X = COCH3
R⁴—HN—C(H)=C(X)(COR⁵)
R⁴ = phenyl-(Y)ₙ

| Y | R⁵ | n | Position |
|---|----|---|----------|
| C₁₈H₃₇OCO | CH₃O | 2 | ortho/para |
| C₃H₇OCO | C₂H₅O | 1 | para |
| C₃H₇OCO | C₂H₅O | 1 | meta |
| C₃H₇OCO | C₂H₅O | 1 | ortho |
| C₃H₇OCO | C₂H₅O | 2 | ortho/para |
| C₄H₉OCO | C₂H₅O | 1 | para |
| C₄H₉OCO | C₂H₅O | 1 | meta |
| C₄H₉OCO | C₂H₅O | 1 | ortho |
| C₄H₉OCO | C₂H₅O | 2 | ortho/para |
| C₅H₁₁OCO | C₂H₅O | 1 | para |
| C₅H₁₁OCO | C₂H₅O | 1 | meta |
| C₅H₁₁OCO | C₂H₅O | 1 | ortho |
| C₅H₁₁OCO | C₂H₅O | 2 | ortho/para |
| C₆H₁₃OCO | C₂H₅O | 1 | para |
| C₆H₁₃OCO | C₂H₅O | 1 | meta |
| C₆H₁₃OCO | C₂H₅O | 1 | ortho |
| C₆H₁₃OCO | C₂H₅O | 2 | ortho/para |
| C₈H₁₇OCO | C₂H₅O | 1 | para |
| C₈H₁₇OCO | C₂H₅O | 1 | meta |
| C₈H₁₇OCO | C₂H₅O | 1 | ortho |
| C₈H₁₇OCO | C₂H₅O | 2 | ortho/para |
| C₁₂H₂₅OCO | C₂H₅O | 1 | para |
| C₁₂H₂₅OCO | C₂H₅O | 1 | meta |
| C₁₂H₂₅OCO | C₂H₅O | 1 | ortho |
| C₁₂H₂₅OCO | C₂H₅O | 2 | ortho/para |
| C₁₃H₂₇OCO | C₂H₅O | 1 | para |
| C₁₃H₂₇OCO | C₂H₅O | 1 | meta |
| C₁₃H₂₇OCO | C₂H₅O | 1 | ortho |
| C₁₃H₂₇OCO | C₂H₅O | 2 | ortho/para |
| C₁₄H₂₉OCO | C₂H₅O | 1 | para |
| C₁₄H₂₉OCO | C₂H₅O | 1 | meta |
| C₁₄H₂₉OCO | C₂H₅O | 1 | ortho |
| C₁₄H₂₉OCO | C₂H₅O | 2 | ortho/para |
| C₁₅H₃₁OCO | C₂H₅O | 1 | para |
| C₁₅H₃₁OCO | C₂H₅O | 1 | meta |
| C₁₅H₃₁OCO | C₂H₅O | 1 | ortho |
| C₁₅H₃₁OCO | C₂H₅O | 2 | ortho/para |
| C₁₆H₃₃OCO | C₂H₅O | 1 | para |
| C₁₆H₃₃OCO | C₂H₅O | 1 | meta |
| C₁₆H₃₃OCO | C₂H₅O | 1 | ortho |
| C₁₆H₃₃OCO | C₂H₅O | 2 | ortho/para |
| C₁₇H₃₅OCO | C₂H₅O | 1 | para |
| C₁₇H₃₅OCO | C₂H₅O | 1 | meta |
| C₁₇H₃₅OCO | C₂H₅O | 1 | ortho |
| C₁₇H₃₅OCO | C₂H₅O | 2 | ortho/para |
| C₁₈H₃₇OCO | C₂H₅O | 1 | para |
| C₁₈H₃₇OCO | C₂H₅O | 1 | meta |
| C₁₈H₃₇OCO | C₂H₅O | 1 | ortho |
| C₁₈H₃₇OCO | C₂H₅O | 2 | ortho/para |
| C₃H₇OCO | C₃H₇O | 1 | para |
| C₃H₇OCO | C₃H₇O | 1 | meta |
| C₃H₇OCO | C₃H₇O | 1 | ortho |
| C₃H₇OCO | C₃H₇O | 2 | ortho/para |
| C₄H₉OCO | C₃H₇O | 1 | para |
| C₄H₉OCO | C₃H₇O | 1 | meta |
| C₄H₉OCO | C₃H₇O | 1 | ortho |
| C₄H₉OCO | C₃H₇O | 2 | ortho/para |
| C₅H₁₁OCO | C₃H₇O | 1 | para |
| C₅H₁₁OCO | C₃H₇O | 1 | meta |
| C₅H₁₁OCO | C₃H₇O | 1 | ortho |
| C₅H₁₁OCO | C₃H₇O | 2 | ortho/para |
| C₆H₁₃OCO | C₃H₇O | 1 | para |
| C₆H₁₃OCO | C₃H₇O | 1 | meta |
| C₆H₁₃OCO | C₃H₇O | 1 | ortho |
| C₆H₁₃OCO | C₃H₇O | 2 | ortho/para |
| C₈H₁₇OCO | C₃H₇O | 1 | para |
| C₈H₁₇OCO | C₃H₇O | 1 | meta |
| C₈H₁₇OCO | C₃H₇O | 1 | ortho |
| C₈H₁₇OCO | C₃H₇O | 2 | ortho/para |
| C₁₂H₂₅OCO | C₃H₇O | 1 | para |
| C₁₂H₂₅OCO | C₃H₇O | 1 | meta |
| C₁₂H₂₅OCO | C₃H₇O | 1 | ortho |
| C₁₂H₂₅OCO | C₃H₇O | 2 | ortho/para |
| C₁₃H₂₇OCO | C₃H₇O | 1 | para |
| C₁₃H₂₇OCO | C₃H₇O | 1 | meta |
| C₁₃H₂₇OCO | C₃H₇O | 1 | ortho |
| C₁₃H₂₇OCO | C₃H₇O | 2 | ortho/para |
| C₁₄H₂₉OCO | C₃H₇O | 1 | para |
| C₁₄H₂₉OCO | C₃H₇O | 1 | meta |
| C₁₄H₂₉OCO | C₃H₇O | 1 | ortho |
| C₁₄H₂₉OCO | C₃H₇O | 2 | ortho/para |
| C₁₅H₃₁OCO | C₃H₇O | 1 | para |
| C₁₅H₃₁OCO | C₃H₇O | 1 | meta |
| C₁₅H₃₁OCO | C₃H₇O | 1 | ortho |
| C₁₅H₃₁OCO | C₃H₇O | 2 | ortho/para |
| C₁₆H₃₃OCO | C₃H₇O | 1 | para |
| C₁₆H₃₃OCO | C₃H₇O | 1 | meta |
| C₁₆H₃₃OCO | C₃H₇O | 1 | ortho |
| C₁₆H₃₃OCO | C₃H₇O | 2 | ortho/para |
| C₁₇H₃₅OCO | C₃H₇O | 1 | para |
| C₁₇H₃₅OCO | C₃H₇O | 1 | meta |
| C₁₇H₃₅OCO | C₃H₇O | 1 | ortho |
| C₁₇H₃₅OCO | C₃H₇O | 2 | ortho/para |
| C₁₈H₃₇OCO | C₃H₇O | 1 | para |
| C₁₈H₃₇OCO | C₃H₇O | 1 | meta |
| C₁₈H₃₇OCO | C₃H₇O | 1 | ortho |
| C₁₈H₃₇OCO | C₃H₇O | 2 | ortho/para |
| C₃H₇OCO | C₄H₉O | 1 | para |
| C₃H₇OCO | C₄H₉O | 1 | meta |
| C₃H₇OCO | C₄H₉O | 1 | ortho |
| C₃H₇OCO | C₄H₉O | 2 | ortho/para |
| C₄H₉OCO | C₄H₉O | 1 | para |
| C₄H₉OCO | C₄H₉O | 1 | meta |
| C₄H₉OCO | C₄H₉O | 1 | ortho |
| C₄H₉OCO | C₄H₉O | 2 | ortho/para |
| C₅H₁₁OCO | C₄H₉O | 1 | para |
| C₅H₁₁OCO | C₄H₉O | 1 | meta |
| C₅H₁₁OCO | C₄H₉O | 1 | ortho |
| C₅H₁₁OCO | C₄H₉O | 2 | ortho/para |
| C₆H₁₃OCO | C₄H₉O | 1 | para |
| C₆H₁₃OCO | C₄H₉O | 1 | meta |
| C₆H₁₃OCO | C₄H₉O | 1 | ortho |
| C₆H₁₃OCO | C₄H₉O | 2 | ortho/para |
| C₈H₁₇OCO | C₄H₉O | 1 | para |
| C₈H₁₇OCO | C₄H₉O | 1 | meta |
| C₈H₁₇OCO | C₄H₉O | 1 | ortho |
| C₈H₁₇OCO | C₄H₉O | 2 | ortho/para |
| C₁₂H₂₅OCO | C₄H₉O | 1 | para |
| C₁₂H₂₅OCO | C₄H₉O | 1 | meta |
| C₁₂H₂₅OCO | C₄H₉O | 1 | ortho |
| C₁₂H₂₅OCO | C₄H₉O | 2 | ortho/para |
| C₁₃H₂₇OCO | C₄H₉O | 1 | para |
| C₁₃H₂₇OCO | C₄H₉O | 1 | meta |
| C₁₃H₂₇OCO | C₄H₉O | 1 | ortho |
| C₁₃H₂₇OCO | C₄H₉O | 2 | ortho/para |
| C₁₄H₂₉OCO | C₄H₉O | 1 | para |
| C₁₄H₂₉OCO | C₄H₉O | 1 | meta |
| C₁₄H₂₉OCO | C₄H₉O | 1 | ortho |
| C₁₄H₂₉OCO | C₄H₉O | 2 | ortho/para |
| C₁₅H₃₁OCO | C₄H₉O | 1 | para |
| C₁₅H₃₁OCO | C₄H₉O | 1 | meta |
| C₁₅H₃₁OCO | C₄H₉O | 1 | ortho |
| C₁₅H₃₁OCO | C₄H₉O | 2 | ortho/para |
| C₁₆H₃₃OCO | C₄H₉O | 1 | para |
| C₁₆H₃₃OCO | C₄H₉O | 1 | meta |
| C₁₆H₃₃OCO | C₄H₉O | 1 | ortho |
| C₁₆H₃₃OCO | C₄H₉O | 2 | ortho/para |
| C₁₇H₃₅OCO | C₄H₉O | 1 | para |
| C₁₇H₃₅OCO | C₄H₉O | 1 | meta |
| C₁₇H₃₅OCO | C₄H₉O | 1 | ortho |

TABLE 1-continued

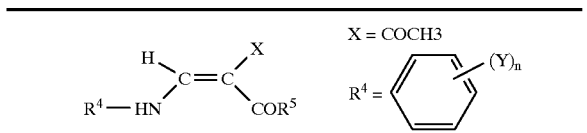

X = COCH3

R⁴ = [phenyl with (Y)$_n$]

| Y | R⁵ | n | Position |
|---|---|---|---|
| $C_{17}H_{35}OCO$ | $C_4H_9O$ | 2 | ortho/para |
| $C_{18}H_{37}OCO$ | $C_4H_9O$ | 1 | para |
| $C_{18}H_{37}OCO$ | $C_4H_9O$ | 1 | meta |
| $C_{18}H_{37}OCO$ | $C_4H_9O$ | 1 | ortho |
| $C_{18}H_{37}OCO$ | $C_4H_9O$ | 2 | ortho/para |
| $C_3H_7OCO$ | $C_5H_{11}O$ | 1 | para |
| $C_3H_7OCO$ | $C_5H_{11}O$ | 1 | meta |
| $C_3H_7OCO$ | $C_5H_{11}O$ | 1 | ortho |
| $C_3H_7OCO$ | $C_5H_{11}O$ | 2 | ortho/para |
| $C_4H_9OCO$ | $C_5H_{11}O$ | 1 | para |
| $C_4H_9OCO$ | $C_5H_{11}O$ | 1 | meta |
| $C_4H_9OCO$ | $C_5H_{11}O$ | 1 | ortho |
| $C_4H_9OCO$ | $C_5H_{11}O$ | 2 | ortho/para |
| $C_5H_{11}OCO$ | $C_5H_{11}O$ | 1 | para |
| $C_5H_{11}OCO$ | $C_5H_{11}O$ | 1 | meta |
| $C_5H_{11}OCO$ | $C_5H_{11}O$ | 1 | ortho |
| $C_5H_{11}OCO$ | $C_5H_{11}O$ | 2 | ortho/para |
| $C_6H_{13}OCO$ | $C_5H_{11}O$ | 1 | para |
| $C_6H_{13}OCO$ | $C_5H_{11}O$ | 1 | meta |
| $C_6H_{13}OCO$ | $C_5H_{11}O$ | 1 | ortho |
| $C_6H_{13}OCO$ | $C_5H_{11}O$ | 2 | ortho/para |
| $C_8H_{17}OCO$ | $C_5H_{11}O$ | 1 | para |
| $C_8H_{17}OCO$ | $C_5H_{11}O$ | 1 | meta |
| $C_8H_{17}OCO$ | $C_5H_{11}O$ | 1 | ortho |
| $C_8H_{17}OCO$ | $C_5H_{11}O$ | 2 | ortho/para |
| $C_{12}H_{25}OCO$ | $C_5H_{11}O$ | 1 | para |
| $C_{12}H_{25}OCO$ | $C_5H_{11}O$ | 1 | meta |
| $C_{12}H_{25}OCO$ | $C_5H_{11}O$ | 1 | ortho |
| $C_{12}H_{25}OCO$ | $C_5H_{11}O$ | 2 | ortho/para |
| $C_{13}H_{27}OCO$ | $C_5H_{11}O$ | 1 | para |
| $C_{13}H_{27}OCO$ | $C_5H_{11}O$ | 1 | meta |
| $C_{13}H_{27}OCO$ | $C_5H_{11}O$ | 1 | ortho |
| $C_{13}H_{27}OCO$ | $C_5H_{11}O$ | 2 | ortho/para |
| $C_{14}H_{29}OCO$ | $C_5H_{11}O$ | 1 | para |
| $C_{14}H_{29}OCO$ | $C_5H_{11}O$ | 1 | meta |
| $C_{14}H_{29}OCO$ | $C_5H_{11}O$ | 1 | ortho |
| $C_{14}H_{29}OCO$ | $C_5H_{11}O$ | 2 | ortho/para |
| $C_{15}H_{31}OCO$ | $C_5H_{11}O$ | 1 | para |
| $C_{15}H_{31}OCO$ | $C_5H_{11}O$ | 1 | meta |
| $C_{15}H_{31}OCO$ | $C_5H_{11}O$ | 1 | ortho |
| $C_{15}H_{31}OCO$ | $C_5H_{11}O$ | 2 | ortho/para |
| $C_{16}H_{33}OCO$ | $C_5H_{11}O$ | 1 | para |
| $C_{16}H_{33}OCO$ | $C_5H_{11}O$ | 1 | meta |
| $C_{16}H_{33}OCO$ | $C_5H_{11}O$ | 1 | ortho |
| $C_{16}H_{33}OCO$ | $C_5H_{11}O$ | 2 | ortho/para |
| $C_{17}H_{35}OCO$ | $C_5H_{11}O$ | 1 | para |
| $C_{17}H_{35}OCO$ | $C_5H_{11}O$ | 1 | meta |
| $C_{17}H_{35}OCO$ | $C_5H_{11}O$ | 1 | ortho |
| $C_{17}H_{35}OCO$ | $C_5H_{11}O$ | 2 | ortho/para |
| $C_{18}H_{37}OCO$ | $C_5H_{11}O$ | 1 | para |
| $C_{18}H_{37}OCO$ | $C_5H_{11}O$ | 1 | meta |
| $C_{18}H_{37}OCO$ | $C_5H_{11}O$ | 1 | ortho |
| $C_{18}H_{37}OCO$ | $C_5H_{11}O$ | 2 | ortho/para |
| $C_3H_7OCO$ | $C_6H_{13}O$ | 1 | para |
| $C_3H_7OCO$ | $C_6H_{13}O$ | 1 | meta |
| $C_3H_7OCO$ | $C_6H_{13}O$ | 1 | ortho |
| $C_3H_7OCO$ | $C_6H_{13}O$ | 2 | ortho/para |
| $C_4H_9OCO$ | $C_6H_{13}O$ | 1 | para |
| $C_4H_9OCO$ | $C_6H_{13}O$ | 1 | meta |
| $C_4H_9OCO$ | $C_6H_{13}O$ | 1 | ortho |
| $C_4H_9OCO$ | $C_6H_{13}O$ | 2 | ortho/para |
| $C_5H_{11}OCO$ | $C_6H_{13}O$ | 1 | para |
| $C_5H_{11}OCO$ | $C_6H_{13}O$ | 1 | meta |
| $C_5H_{11}OCO$ | $C_6H_{13}O$ | 1 | ortho |
| $C_5H_{11}OCO$ | $C_6H_{13}O$ | 2 | ortho/para |
| $C_6H_{13}OCO$ | $C_6H_{13}O$ | 1 | para |
| $C_6H_{13}OCO$ | $C_6H_{13}O$ | 1 | meta |
| $C_6H_{13}OCO$ | $C_6H_{13}O$ | 1 | ortho |
| $C_6H_{13}OCO$ | $C_6H_{13}O$ | 2 | ortho/para |
| $C_8H_{17}OCO$ | $C_6H_{13}O$ | 1 | para |
| $C_8H_{17}OCO$ | $C_6H_{13}O$ | 1 | meta |
| $C_8H_{17}OCO$ | $C_6H_{13}O$ | 1 | ortho |
| $C_8H_{17}OCO$ | $C_6H_{13}O$ | 2 | ortho/para |
| $C_{12}H_{25}OCO$ | $C_6H_{13}O$ | 1 | para |
| $C_{12}H_{25}OCO$ | $C_6H_{13}O$ | 1 | meta |
| $C_{12}H_{25}OCO$ | $C_6H_{13}O$ | 1 | ortho |
| $C_{12}H_{25}OCO$ | $C_6H_{13}O$ | 2 | ortho/para |
| $C_{13}H_{27}OCO$ | $C_6H_{13}O$ | 1 | para |
| $C_{13}H_{27}OCO$ | $C_6H_{13}O$ | 1 | meta |
| $C_{13}H_{27}OCO$ | $C_6H_{13}O$ | 1 | ortho |
| $C_{13}H_{27}OCO$ | $C_6H_{13}O$ | 2 | ortho/para |
| $C_{14}H_{29}OCO$ | $C_6H_{13}O$ | 1 | para |
| $C_{14}H_{29}OCO$ | $C_6H_{13}O$ | 1 | meta |
| $C_{14}H_{29}OCO$ | $C_6H_{13}O$ | 1 | ortho |
| $C_{14}H_{29}OCO$ | $C_6H_{13}O$ | 2 | ortho/para |
| $C_{15}H_{31}OCO$ | $C_6H_{13}O$ | 1 | para |
| $C_{15}H_{31}OCO$ | $C_6H_{13}O$ | 1 | meta |
| $C_{15}H_{31}OCO$ | $C_6H_{13}O$ | 1 | ortho |
| $C_{15}H_{31}OCO$ | $C_6H_{13}O$ | 2 | ortho/para |
| $C_{16}H_{33}OCO$ | $C_6H_{13}O$ | 1 | para |
| $C_{16}H_{33}OCO$ | $C_6H_{13}O$ | 1 | meta |
| $C_{16}H_{33}OCO$ | $C_6H_{13}O$ | 1 | ortho |
| $C_{16}H_{33}OCO$ | $C_6H_{13}O$ | 2 | ortho/para |
| $C_{17}H_{35}OCO$ | $C_6H_{13}O$ | 1 | para |
| $C_{17}H_{35}OCO$ | $C_6H_{13}O$ | 1 | meta |
| $C_{17}H_{35}OCO$ | $C_6H_{13}O$ | 1 | ortho |
| $C_{17}H_{35}OCO$ | $C_6H_{13}O$ | 2 | ortho/para |
| $C_{18}H_{37}OCO$ | $C_6H_{13}O$ | 1 | para |
| $C_{18}H_{37}OCO$ | $C_6H_{13}O$ | 1 | meta |
| $C_{18}H_{37}OCO$ | $C_6H_{13}O$ | 1 | ortho |
| $C_{18}H_{37}OCO$ | $C_6H_{13}O$ | 2 | ortho/para |
| $C_3H_7OCO$ | $C_7H_{15}O$ | 1 | para |
| $C_3H_7OCO$ | $C_7H_{15}O$ | 1 | meta |
| $C_3H_7OCO$ | $C_7H_{15}O$ | 1 | ortho |
| $C_3H_7OCO$ | $C_7H_{15}O$ | 2 | ortho/para |
| $C_4H_9OCO$ | $C_7H_{15}O$ | 1 | para |
| $C_4H_9OCO$ | $C_7H_{15}O$ | 1 | meta |
| $C_4H_9OCO$ | $C_7H_{15}O$ | 1 | ortho |
| $C_4H_9OCO$ | $C_7H_{15}O$ | 2 | ortho/para |
| $C_5H_{11}OCO$ | $C_7H_{15}O$ | 1 | para |
| $C_5H_{11}OCO$ | $C_7H_{15}O$ | 1 | meta |
| $C_5H_{11}OCO$ | $C_7H_{15}O$ | 1 | ortho |
| $C_5H_{11}OCO$ | $C_7H_{15}O$ | 2 | ortho/para |
| $C_6H_{13}OCO$ | $C_7H_{15}O$ | 1 | para |
| $C_6H_{13}OCO$ | $C_7H_{15}O$ | 1 | meta |
| $C_6H_{13}OCO$ | $C_7H_{15}O$ | 1 | ortho |
| $C_6H_{13}OCO$ | $C_7H_{15}O$ | 2 | ortho/para |
| $C_8H_{17}OCO$ | $C_7H_{15}O$ | 1 | para |
| $C_8H_{17}OCO$ | $C_7H_{15}O$ | 1 | meta |
| $C_8H_{17}OCO$ | $C_7H_{15}O$ | 1 | ortho |
| $C_8H_{17}OCO$ | $C_7H_{15}O$ | 2 | ortho/para |
| $C_{12}H_{25}OCO$ | $C_7H_{15}O$ | 1 | para |
| $C_{12}H_{25}OCO$ | $C_7H_{15}O$ | 1 | meta |
| $C_{12}H_{25}OCO$ | $C_7H_{15}O$ | 1 | ortho |
| $C_{12}H_{25}OCO$ | $C_7H_{15}O$ | 2 | ortho/para |
| $C_{13}H_{27}OCO$ | $C_7H_{15}O$ | 1 | para |
| $C_{13}H_{27}OCO$ | $C_7H_{15}O$ | 1 | meta |
| $C_{13}H_{27}OCO$ | $C_7H_{15}O$ | 1 | ortho |
| $C_{13}H_{27}OCO$ | $C_7H_{15}O$ | 2 | ortho/para |
| $C_{14}H_{29}OCO$ | $C_7H_{15}O$ | 1 | para |
| $C_{14}H_{29}OCO$ | $C_7H_{15}O$ | 1 | meta |
| $C_{14}H_{29}OCO$ | $C_7H_{15}O$ | 1 | ortho |
| $C_{14}H_{29}OCO$ | $C_7H_{15}O$ | 2 | ortho/para |
| $C_{15}H_{31}OCO$ | $C_7H_{15}O$ | 1 | para |
| $C_{15}H_{31}OCO$ | $C_7H_{15}O$ | 1 | meta |
| $C_{15}H_{31}OCO$ | $C_7H_{15}O$ | 1 | ortho |
| $C_{15}H_{31}OCO$ | $C_7H_{15}O$ | 2 | ortho/para |
| $C_{16}H_{33}OCO$ | $C_7H_{15}O$ | 1 | para |
| $C_{16}H_{33}OCO$ | $C_7H_{15}O$ | 1 | meta |
| $C_{16}H_{33}OCO$ | $C_7H_{15}O$ | 1 | ortho |

TABLE 1-continued

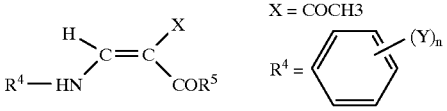

X = COCH3

| Y | R⁵ | n | Position |
|---|---|---|---|
| C₁₆H₃₃OCO | C₇H₁₅O | 2 | orthb|para |
| C₁₇H₃₅OCO | C₇H₁₅O | 1 | para |
| C₁₇H₃₅OCO | C₇H₁₅O | 1 | meta |
| C₁₇H₃₅OCO | C₇H₁₅O | 1 | ortho |
| C₁₇H₃₅OCO | C₇H₁₅O | 2 | ortho/para |
| C₁₈H₃₇OCO | C₇H₁₅O | 1 | para |
| C₁₈H₃₇OCO | C₇H₁₅O | 1 | meta |
| C₁₈H₃₇OCO | C₇H₁₅O | 1 | ortho |
| C₁₈H₃₇OCO | C₇H₁₅O | 2 | ortho/para |
| C₃H₇OCO | C₈H₁₇O | 1 | para |
| C₃H₇OCO | C₈H₁₇O | 1 | meta |
| C₃H₇OCO | C₈H₁₇O | 1 | ortho |
| C₃H₇OCO | C₈H₁₇O | 2 | ortho/para |
| C₄H₉OCO | C₈H₁₇O | 1 | para |
| C₄H₉OCO | C₈H₁₇O | 1 | meta |
| C₄H₉OCO | C₈H₁₇O | 1 | ortho |
| C₄H₉OCO | C₈H₁₇O | 2 | ortho/para |
| C₅H₁₁OCO | C₈H₁₇O | 1 | para |
| C₅H₁₁OCO | C₈H₁₇O | 1 | meta |
| C₅H₁₁OCO | C₈H₁₇O | 1 | ortho |
| C₅H₁₁OCO | C₈H₁₇O | 2 | ortho/para |
| C₆H₁₃OCO | C₈H₁₇O | 1 | para |
| C₆H₁₃OCO | C₈H₁₇O | 1 | meta |
| C₆H₁₃OCO | C₈H₁₇O | 1 | ortho |
| C₆H₁₃OCO | C₈H₁₇O | 2 | ortho/para |
| C₈H₁₇OCO | C₈H₁₇O | 1 | para |
| C₈H₁₇OCO | C₈H₁₇O | 1 | meta |
| C₈H₁₇OCO | C₈H₁₇O | 1 | ortho |
| C₈H₁₇OCO | C₈H₁₇O | 2 | ortho/para |
| C₁₂H₂₅OCO | C₈H₁₇O | 1 | para |
| C₁₂H₂₅OCO | C₈H₁₇O | 1 | meta |
| C₁₂H₂₅OCO | C₈H₁₇O | 1 | ortho |
| C₁₂H₂₅OCO | C₈H₁₇O | 2 | ortho/para |
| C₁₃H₂₇OCO | C₈H₁₇O | 1 | para |
| C₁₃H₂₇OCO | C₈H₁₇O | 1 | meta |
| C₁₃H₂₇OCO | C₈H₁₇O | 1 | ortho |
| C₁₃H₂₇OCO | C₈H₁₇O | 2 | ortho/para |
| C₁₄H₂₉OCO | C₈H₁₇O | 1 | para |
| C₁₄H₂₉OCO | C₈H₁₇O | 1 | meta |
| C₁₄H₂₉OCO | C₈H₁₇O | 1 | ortho |
| C₁₄H₂₉OCO | C₈H₁₇O | 2 | ortho/para |
| C₁₅H₃₁OCO | C₈H₁₇O | 1 | para |
| C₁₅H₃₁OCO | C₈H₁₇O | 1 | meta |
| C₁₅H₃₁OCO | C₈H₁₇O | 1 | ortho |
| C₁₅H₃₁OCO | C₈H₁₇O | 2 | ortho/para |
| C₁₆H₃₃OCO | C₈H₁₇O | 1 | para |
| C₁₆H₃₃OCO | C₈H₁₇O | 1 | meta |
| C₁₆H₃₃OCO | C₈H₁₇O | 1 | ortho |
| C₁₆H₃₃OCO | C₈H₁₇O | 2 | ortho/para |
| C₁₇H₃₅OCO | C₈H₁₇O | 1 | para |
| C₁₇H₃₅OCO | C₈H₁₇O | 1 | meta |
| C₁₇H₃₅OCO | C₈H₁₇O | 1 | ortho |
| C₁₇H₃₅OCO | C₈H₁₇O | 2 | ortho/para |
| C₁₈H₃₇OCO | C₈H₁₇O | 1 | para |
| C₁₈H₃₇OCO | C₈H₁₇O | 1 | meta |
| C₁₈H₃₇OCO | C₈H₁₇O | 1 | ortho |
| C₁₈H₃₇OCO | C₈H₁₇O | 2 | ortho/para |
| C₃H₇OCO | C₁₂H₂₅O | 1 | para |
| C₃H₇OCO | C₁₂H₂₅O | 1 | meta |
| C₃H₇OCO | C₁₂H₂₅O | 1 | ortho |
| C₃H₇OCO | C₁₂H₂₅O | 2 | ortho/para |
| C₄H₉OCO | C₁₂H₂₅O | 1 | para |
| C₄H₉OCO | C₁₂H₂₅O | 1 | meta |
| C₄H₉OCO | C₁₂H₂₅O | 1 | ortho |
| C₄H₉OCO | C₁₂H₂₅O | 2 | ortho/para |
| C₅H₁₁OCO | C₁₂H₂₅O | 1 | para |
| C₅H₁₁OCO | C₁₂H₂₅O | 1 | meta |
| C₅H₁₁OCO | C₁₂H₂₅O | 1 | ortho |
| C₅H₁₁OCO | C₁₂H₂₅O | 2 | ortho/para |
| C₆H₁₃OCO | C₁₂H₂₅O | 1 | para |

TABLE 1-continued

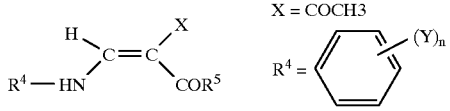

X = COCH3

| Y | R⁵ | n | Position |
|---|---|---|---|
| C₆H₁₃OCO | C₁₂H₂₅O | 1 | meta |
| C₆H₁₃OCO | C₁₂H₂₅O | 1 | ortho |
| C₆H₁₃OCO | C₁₂H₂₅O | 2 | ortho/para |
| C₈H₁₇OCO | C₁₂H₂₅O | 1 | para |
| C₈H₁₇OCO | C₁₂H₂₅O | 1 | meta |
| C₈H₁₇OCO | C₁₂H₂₅O | 1 | ortho |
| C₈H₁₇OCO | C₁₂H₂₅O | 2 | ortho/para |
| C₁₂H₂₅OCO | C₁₂H₂₅O | 1 | para |
| C₁₂H₂₅OCO | C₁₂H₂₅O | 1 | meta |
| C₁₂H₂₅OCO | C₁₂H₂₅O | 1 | ortho |
| C₁₂H₂₅OCO | C₁₂H₂₅O | 2 | ortho/para |
| C₁₃H₂₇OCO | C₁₂H₂₅O | 1 | para |
| C₁₃H₂₇OCO | C₁₂H₂₅O | 1 | meta |
| C₁₃H₂₇OCO | C₁₂H₂₅O | 1 | ortho |
| C₁₃H₂₇OCO | C₁₂H₂₅O | 2 | ortho/para |
| C₁₄H₂₉OCO | C₁₂H₂₅O | 1 | para |
| C₁₄H₂₉OCO | C₁₂H₂₅O | 1 | meta |
| C₁₄H₂₉OCO | C₁₂H₂₅O | 1 | ortho |
| C₁₄H₂₉OCO | C₁₂H₂₅O | 2 | ortho/para |
| C₁₅H₃₁OCO | C₁₂H₂₅O | 1 | para |
| C₁₅H₃₁OCO | C₁₂H₂₅O | 1 | meta |
| C₁₅H₃₁OCO | C₁₂H₂₅O | 1 | ortho |
| C₁₅H₃₁OCO | C₁₂H₂₅O | 2 | ortho/para |
| C₁₆H₃₃OCO | C₁₂H₂₅O | 1 | para |
| C₁₆H₃₃OCO | C₁₂H₂₅O | 1 | meta |
| C₁₆H₃₃OCO | C₁₂H₂₅O | 1 | ortho |
| C₁₆H₃₃OCO | C₁₂H₂₅O | 2 | ortho/para |
| C₁₇H₃₅OCO | C₁₂H₂₅O | 1 | para |
| C₁₇H₃₅OCO | C₁₂H₂₅O | 1 | meta |
| C₁₇H₃₅OCO | C₁₂H₂₅O | 1 | ortho |
| C₁₇H₃₅OCO | C₁₂H₂₅O | 2 | ortho/para |
| C₁₈H₃₇OCO | C₁₂H₂₅O | 1 | para |
| C₁₈H₃₇OCO | C₁₂H₂₅O | 1 | meta |
| C₁₈H₃₇OCO | C₁₂H₂₅O | 1 | ortho |
| C₁₈H₃₇OCO | C₁₂H₂₅O | 2 | ortho/para |
| C₃H₇OCO | C₁₄H₂₉O | 1 | para |
| C₃H₇OCO | C₁₄H₂₉O | 1 | meta |
| C₃H₇OCO | C₁₄H₂₉O | 1 | ortho |
| C₃H₇OCO | C₁₄H₂₉O | 2 | ortho/para |
| C₄H₉OCO | C₁₄H₂₉O | 1 | para |
| C₄H₉OCO | C₁₄H₂₉O | 1 | meta |
| C₄H₉OCO | C₁₄H₂₉O | 1 | ortho |
| C₄H₉OCO | C₁₄H₂₉O | 2 | ortho/para |
| C₅H₁₁OCO | C₁₄H₂₉O | 1 | para |
| C₅H₁₁OCO | C₁₄H₂₉O | 1 | meta |
| C₅H₁₁OCO | C₁₄H₂₉O | 1 | ortho |
| C₅H₁₁OCO | C₁₄H₂₉O | 2 | ortho/para |
| C₆H₁₃OCO | C₁₄H₂₉O | 1 | para |
| C₆H₁₃OCO | C₁₄H₂₉O | 1 | meta |
| C₆H₁₃OCO | C₁₄H₂₉O | 1 | ortho |
| C₆H₁₃OCO | C₁₄H₂₉O | 2 | ortho/para |
| C₈H₁₇OCO | C₁₄H₂₉O | 1 | para |
| C₈H₁₇OCO | C₁₄H₂₉O | 1 | meta |
| C₈H₁₇OCO | C₁₄H₂₉O | 1 | ortho |
| C₈H₁₇OCO | C₁₄H₂₉O | 2 | ortho/para |
| C₁₂H₂₅OCO | C₁₄H₂₉O | 1 | para |
| C₁₂H₂₅OCO | C₁₄H₂₉O | 1 | meta |
| C₁₂H₂₅OCO | C₁₄H₂₉O | 1 | ortho |
| C₁₂H₂₅OCO | C₁₄H₂₉O | 2 | ortho/para |
| C₁₃H₂₇OCO | C₁₄H₂₉O | 1 | para |
| C₁₃H₂₇OCO | C₁₄H₂₉O | 1 | meta |
| C₁₃H₂₇OCO | C₁₄H₂₉O | 1 | ortho |
| C₁₃H₂₇OCO | C₁₄H₂₉O | 2 | ortho/para |
| C₁₄H₂₉OCO | C₁₄H₂₉O | 1 | para |
| C₁₄H₂₉OCO | C₁₄H₂₉O | 1 | meta |
| C₁₄H₂₉OCO | C₁₄H₂₉O | 1 | ortho |
| C₁₄H₂₉OCO | C₁₄H₂₉O | 2 | ortho/para |
| C₁₅H₃₁OCO | C₁₄H₂₉O | 1 | para |
| C₁₅H₃₁OCO | C₁₄H₂₉O | 1 | meta |
| C₁₅H₃₁OCO | C₁₄H₂₉O | 1 | ortho |

TABLE 1-continued

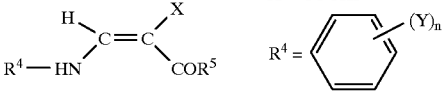

X = COCH3

| Y | R⁵ | n | Position |
|---|----|----|----------|
| $C_{15}H_{31}OCO$ | $C_{14}H_{29}O$ | 2 | ortho/para |
| $C_{16}H_{33}OCO$ | $C_{14}H_{29}O$ | 1 | para |
| $C_{16}H_{33}OCO$ | $C_{14}H_{29}O$ | 1 | meta |
| $C_{16}H_{33}OCO$ | $C_{14}H_{29}O$ | 1 | ortho |
| $C_{16}H_{33}OCO$ | $C_{14}H_{29}O$ | 2 | ortho/para |
| $C_{17}H_{35}OCO$ | $C_{14}H_{29}O$ | 1 | para |
| $C_{17}H_{35}OCO$ | $C_{14}H_{29}O$ | 1 | meta |
| $C_{17}H_{35}OCO$ | $C_{14}H_{29}O$ | 1 | ortho |
| $C_{17}H_{35}OCO$ | $C_{14}H_{29}O$ | 2 | ortho/para |
| $C_{18}H_{37}OCO$ | $C_{14}H_{29}O$ | 1 | para |
| $C_{18}H_{37}OCO$ | $C_{14}H_{29}O$ | 1 | meta |
| $C_{18}H_{37}OCO$ | $C_{14}H_{29}O$ | 1 | ortho |
| $C_{18}H_{37}OCO$ | $C_{14}H_{29}O$ | 2 | ortho/para |
| $C_3H_7OCO$ | $C_{16}H_{33}O$ | 1 | para |
| $C_3H_7OCO$ | $C_{16}H_{33}O$ | 1 | meta |
| $C_3H_7OCO$ | $C_{16}H_{33}O$ | 1 | ortho |
| $C_3H_7OCO$ | $C_{16}H_{33}O$ | 2 | ortho/para |
| $C_4H_9OCO$ | $C_{16}H_{33}O$ | 1 | para |
| $C_4H_9OCO$ | $C_{16}H_{33}O$ | 1 | meta |
| $C_4H_9OCO$ | $C_{16}H_{33}O$ | 1 | ortho |
| $C_4H_9OCO$ | $C_{16}H_{33}O$ | 2 | ortho/para |
| $C_5H_{11}OCO$ | $C_{16}H_{33}O$ | 1 | para |
| $C_5H_{11}OCO$ | $C_{16}H_{33}O$ | 1 | meta |
| $C_5H_{11}OCO$ | $C_{16}H_{33}O$ | 1 | ortho |
| $C_5H_{11}OCO$ | $C_{16}H_{33}O$ | 2 | ortho/para |
| $C_6H_{13}OCO$ | $C_{16}H_{33}O$ | 1 | para |
| $C_6H_{13}OCO$ | $C_{16}H_{33}O$ | 1 | meta |
| $C_6H_{13}OCO$ | $C_{16}H_{33}O$ | 1 | ortho |
| $C_6H_{13}OCO$ | $C_{16}H_{33}O$ | 2 | ortho/para |
| $C_8H_{17}OCO$ | $C_{16}H_{33}O$ | 1 | para |
| $C_8H_{17}OCO$ | $C_{16}H_{33}O$ | 1 | mela |
| $C_8H_{17}OCO$ | $C_{16}H_{33}O$ | 1 | ortho |
| $C_8H_{17}OCO$ | $C_{16}H_{33}O$ | 2 | ortho/para |
| $C_{12}H_{25}OCO$ | $C_{16}H_{33}O$ | 1 | para |
| $C_{12}H_{25}OCO$ | $C_{16}H_{33}O$ | 1 | meta |
| $C_{12}H_{25}OCO$ | $C_{16}H_{33}O$ | 1 | ortho |
| $C_{12}H_{25}OCO$ | $C_{16}H_{33}O$ | 2 | ortho/para |
| $C_{13}H_{27}OCO$ | $C_{16}H_{33}O$ | 1 | para |
| $C_{13}H_{27}OCO$ | $C_{16}H_{33}O$ | 1 | meta |
| $C_{13}H_{27}OCO$ | $C_{16}H_{33}O$ | 1 | ortho |
| $C_{13}H_{27}OCO$ | $C_{16}H_{33}O$ | 2 | ortho/para |
| $C_{14}H_{29}OCO$ | $C_{16}H_{33}O$ | 1 | para |
| $C_{14}H_{29}OCO$ | $C_{16}H_{33}O$ | 1 | meta |
| $C_{14}H_{29}OCO$ | $C_{16}H_{33}O$ | 1 | ortho |
| $C_{14}H_{29}OCO$ | $C_{16}H_{33}O$ | 2 | ortho/para |
| $C_{15}H_{31}OCO$ | $C_{16}H_{33}O$ | 1 | para |
| $C_{15}H_{31}OCO$ | $C_{16}H_{33}O$ | 1 | meta |
| $C_{15}H_{31}OCO$ | $C_{16}H_{33}O$ | 1 | ortho |
| $C_{15}H_{31}OCO$ | $C_{16}H_{33}O$ | 2 | ortho/para |
| $C_{16}H_{33}OCO$ | $C_{16}H_{33}O$ | 1 | para |
| $C_{16}H_{33}OCO$ | $C_{16}H_{33}O$ | 1 | meta |
| $C_{16}H_{33}OCO$ | $C_{16}H_{33}O$ | 1 | ortho |
| $C_{16}H_{33}OCO$ | $C_{16}H_{33}O$ | 2 | ortho/para |
| $C_{17}H_{35}OCO$ | $C_{16}H_{33}O$ | 1 | para |
| $C_{17}H_{35}OCO$ | $C_{16}H_{33}O$ | 1 | meta |
| $C_{17}H_{35}OCO$ | $C_{16}H_{33}O$ | 1 | ortho |
| $C_{17}H_{35}OCO$ | $C_{16}H_{33}O$ | 2 | ortho/para |
| $C_{18}H_{37}OCO$ | $C_{16}H_{33}O$ | 1 | para |
| $C_{18}H_{37}OCO$ | $C_{16}H_{33}O$ | 1 | meta |
| $C_{18}H_{37}OCO$ | $C_{16}H_{33}O$ | 1 | ortho |
| $C_{18}H_{37}OCO$ | $C_{16}H_{33}O$ | 2 | ortho/para |
| $C_3H_7OCO$ | $C_{18}H_{37}O$ | 1 | para |
| $C_3H_7OCO$ | $C_{18}H_{37}O$ | 1 | meta |
| $C_3H_7OCO$ | $C_{18}H_{37}O$ | 1 | ortho |
| $C_3H_7OCO$ | $C_{18}H_{37}O$ | 2 | ortho/para |
| $C_4H_9OCO$ | $C_{18}H_{37}O$ | 1 | para |
| $C_4H_9OCO$ | $C_{18}H_{37}O$ | 1 | meta |
| $C_4H_9OCO$ | $C_{18}H_{37}O$ | 1 | ortho |
| $C_4H_9OCO$ | $C_{18}H_{37}O$ | 2 | ortho/para |
| $C_5H_{11}OCO$ | $C_{18}H_{37}O$ | 1 | para |

TABLE 1-continued

X = COCH3

| Y | R⁵ | n | Position |
|---|----|----|----------|
| $C_5H_{11}OCO$ | $C_{18}H_{37}O$ | 1 | meta |
| $C_5H_{11}OCO$ | $C_{18}H_{37}O$ | 1 | ortho |
| $C_5H_{11}OCO$ | $C_{18}H_{37}O$ | 2 | ortho/para |
| $C_6H_{13}OCO$ | $C_{18}H_{37}O$ | 1 | para |
| $C_6H_{13}OCO$ | $C_{18}H_{37}O$ | 1 | meta |
| $C_6H_{13}OCO$ | $C_{18}H_{37}O$ | 1 | ortho |
| $C_6H_{13}OCO$ | $C_{18}H_{37}O$ | 2 | ortho/para |
| $C_8H_{17}OCO$ | $C_{18}H_{37}O$ | 1 | para |
| $C_8H_{17}OCO$ | $C_{18}H_{37}O$ | 1 | meta |
| $C_8H_{17}OCO$ | $C_{18}H_{37}O$ | 1 | ortho |
| $C_8H_{17}OCO$ | $C_{18}H_{37}O$ | 2 | ortho/para |
| $C_{12}H_{25}OCO$ | $C_{18}H_{37}O$ | 1 | para |
| $C_{12}H_{25}OCO$ | $C_{18}H_{37}O$ | 1 | meta |
| $C_{12}H_{25}OCO$ | $C_{18}H_{37}O$ | 1 | ortho |
| $C_{12}H_{25}OCO$ | $C_{18}H_{37}O$ | 2 | ortho/para |
| $C_{13}H_{27}OCO$ | $C_{18}H_{37}O$ | 1 | para |
| $C_{13}H_{27}OCO$ | $C_{18}H_{37}O$ | 1 | meta |
| $C_{13}H_{27}OCO$ | $C_{18}H_{37}O$ | 1 | ortho |
| $C_{13}H_{27}OCO$ | $C_{18}H_{37}O$ | 2 | ortho/para |
| $C_{14}H_{29}OCO$ | $C_{18}H_{37}O$ | 1 | para |
| $C_{14}H_{29}OCO$ | $C_{18}H_{37}O$ | 1 | meta |
| $C_{14}H_{29}OCO$ | $C_{18}H_{37}O$ | 1 | ortho |
| $C_{14}H_{29}OCO$ | $C_{18}H_{37}O$ | 2 | ortho/para |
| $C_{15}H_{31}OCO$ | $C_{18}H_{37}O$ | 1 | para |
| $C_{15}H_{31}OCO$ | $C_{18}H_{37}O$ | 1 | meta |
| $C_{15}H_{31}OCO$ | $C_{18}H_{37}O$ | 1 | ortho |
| $C_{15}H_{31}OCO$ | $C_{18}H_{37}O$ | 2 | ortho/para |
| $C_{16}H_{33}OCO$ | $C_{18}H_{37}O$ | 1 | para |
| $C_{16}H_{33}OCO$ | $C_{18}H_{37}O$ | 1 | meta |
| $C_{16}H_{33}OCO$ | $C_{18}H_{37}O$ | 1 | ortho |
| $C_{16}H_{33}OCO$ | $C_{18}H_{37}O$ | 2 | ortho/para |
| $C_{17}H_{35}OCO$ | $C_{18}H_{37}O$ | 1 | para |
| $C_{17}H_{35}OCO$ | $C_{18}H_{37}O$ | 1 | meta |
| $C_{17}H_{35}OCO$ | $C_{18}H_{37}O$ | 1 | ortho |
| $C_{17}H_{35}OCO$ | $C_{18}H_{37}O$ | 2 | ortho/para |
| $C_{18}H_{37}OCO$ | $C_{18}H_{37}O$ | 1 | para |
| $C_{18}H_{37}OCO$ | $C_{18}H_{37}O$ | 1 | meta |
| $C_{18}H_{37}OCO$ | $C_{18}H_{37}O$ | 1 | ortho |
| $C_{18}H_{37}OCO$ | $C_{18}H_{37}O$ | 2 | ortho/para |
| $CH_3O$ | $CH_3$ | 1 | para |
| $CH_3O$ | $CH_3$ | 1 | meta |
| $CH_3O$ | $CH_3$ | 1 | ortho |
| $CH_3O$ | $CH_3$ | 2 | ortho/para |
| $C_2H_5O$ | $CH_3$ | 1 | para |
| $C_2H_5O$ | $CH_3$ | 1 | meta |
| $C_2H_5O$ | $CH_3$ | 1 | ortho |
| $C_2H_5O$ | $CH_3$ | 2 | ortho/para |
| $C_3H_7O$ | $CH_3$ | 1 | para |
| $C_3H_7O$ | $CH_3$ | 1 | meta |
| $C_3H_7O$ | $CH_3$ | 1 | ortho |
| $C_3H_7O$ | $CH_3$ | 2 | ortho/para |
| $C_4H_9O$ | $CH_3$ | 1 | para |
| $C_4H_9O$ | $CH_3$ | 1 | meta |
| $C_4H_9O$ | $CH_3$ | 1 | ortho |
| $C_4H_9O$ | $CH_3$ | 2 | ortho/para |
| $C_5H_{11}O$ | $CH_3$ | 1 | para |
| $C_5H_{11}O$ | $CH_3$ | 1 | meta |
| $C_5H_{11}O$ | $CH_3$ | 1 | ortho |
| $C_5H_{11}O$ | $CH_3$ | 2 | ortho/para |
| $C_6H_{13}O$ | $CH_3$ | 1 | para |
| $C_6H_{13}O$ | $CH_3$ | 1 | meta |
| $C_6H_{13}O$ | $CH_3$ | 1 | ortho |
| $C_6H_{13}O$ | $CH_3$ | 2 | ortho/para |
| $C_8H_{17}O$ | $CH_3$ | 1 | para |
| $C_8H_{17}O$ | $CH_3$ | 1 | meta |
| $C_8H_{17}O$ | $CH_3$ | 1 | ortho |
| $C_8H_{17}O$ | $CH_3$ | 2 | ortho/para |
| $C_{12}H_{25}O$ | $CH_3$ | 1 | para |
| $C_{12}H_{25}O$ | $CH_3$ | 1 | meta |
| $C_{12}H_{25}O$ | $CH_3$ | 1 | ortho |

TABLE 1-continued

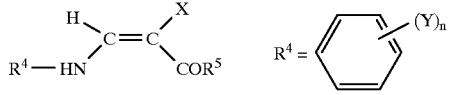

X = COCH3

| Y | $R^5$ | n | Position |
|---|---|---|---|
| $C_{12}H_{25}O$ | $CH_3$ | 2 | ortho/para |
| $C_{13}H_{27}O$ | $CH_3$ | 1 | para |
| $C_{13}H_{27}O$ | $CH_3$ | 1 | meta |
| $C_{13}H_{27}O$ | $CH_3$ | 1 | ortho |
| $C_{13}H_{27}O$ | $CH_3$ | 2 | ortho/para |
| $C_{14}H_{29}O$ | $CH_3$ | 1 | para |
| $C_{14}H_{29}O$ | $CH_3$ | 1 | meta |
| $C_{14}H_{29}O$ | $CH_3$ | 1 | ortho |
| $C_{14}H_{29}O$ | $CH_3$ | 2 | ortho/para |
| $C_{15}H_{31}O$ | $CH_3$ | 1 | para |
| $C_{15}H_{31}O$ | $CH_3$ | 1 | meta |
| $C_{15}H_{31}O$ | $CH_3$ | 1 | ortho |
| $C_{15}H_{31}O$ | $CH_3$ | 2 | ortho/para |
| $C_{16}H_{33}O$ | $CH_3$ | 1 | para |
| $C_{16}H_{33}O$ | $CH_3$ | 1 | meta |
| $C_{16}H_{33}O$ | $CH_3$ | 1 | ortho |
| $C_{16}H_{33}O$ | $CH_3$ | 2 | ortho/para |
| $C_{17}H_{35}O$ | $CH_3$ | 1 | para |
| $C_{17}H_{35}O$ | $CH_3$ | 1 | meta |
| $C_{17}H_{35}O$ | $CH_3$ | 1 | ortho |
| $C_{17}H_{35}O$ | $CH_3$ | 2 | ortho/para |
| $C_{18}H_{37}O$ | $CH_3$ | 1 | para |
| $C_{18}H_{37}O$ | $CH_3$ | 1 | meta |
| $C_{18}H_{37}O$ | $CH_3$ | 1 | ortho |
| $C_{18}H_{37}O$ | $CH_3$ | 2 | ortho/para |
| $CH_3O$ | $C_2H_5$ | 1 | para |
| $CH_3O$ | $C_2H_5$ | 1 | meta |
| $CH_3O$ | $C_2H_5$ | 1 | ortho |
| $CH_3O$ | $C_2H_5$ | 2 | ortho/para |
| $C_2H_5O$ | $C_2H_5$ | 1 | para |
| $C_2H_5O$ | $C_2H_5$ | 1 | meta |
| $C_2H_5O$ | $C_2H_5$ | 1 | ortho |
| $C_2H_5O$ | $C_2H_5$ | 2 | ortho/para |
| $C_3H_7O$ | $C_2H_5$ | 1 | para |
| $C_3H_7O$ | $C_2H_5$ | 1 | meta |
| $C_3H_7O$ | $C_2H_5$ | 1 | ortho |
| $C_3H_7O$ | $C_2H_5$ | 2 | ortho/para |
| $C_4H_9O$ | $C_2H_5$ | 1 | para |
| $C_4H_9O$ | $C_2H_5$ | 1 | meta |
| $C_4H_9O$ | $C_2H_5$ | 1 | ortho |
| $C_4H_9O$ | $C_2H_5$ | 2 | ortho/para |
| $C_5H_{11}O$ | $C_2H_5$ | 1 | para |
| $C_5H_{11}O$ | $C_2H_5$ | 1 | meta |
| $C_5H_{11}O$ | $C_2H_5$ | 1 | ortho |
| $C_5H_{11}O$ | $C_2H_5$ | 2 | ortho/para |
| $C_6H_{13}O$ | $C_2H_5$ | 1 | para |
| $C_6H_{13}O$ | $C_2H_5$ | 1 | meta |
| $C_6H_{13}O$ | $C_2H_5$ | 1 | ortho |
| $C_6H_{13}O$ | $C_2H_5$ | 2 | ortho/para |
| $C_8H_{17}O$ | $C_2H_5$ | 1 | para |
| $C_8H_{17}O$ | $C_2H_5$ | 1 | meta |
| $C_8H_{17}O$ | $C_2H_5$ | 1 | ortho |
| $C_8H_{17}O$ | $C_2H_5$ | 2 | ortho/para |
| $C_{12}H_{25}O$ | $C_2H_5$ | 1 | para |
| $C_{12}H_{25}O$ | $C_2H_5$ | 1 | meta |
| $C_{12}H_{25}O$ | $C_2H_5$ | 1 | ortho |
| $C_{12}H_{25}O$ | $C_2H_5$ | 2 | ortho/para |
| $C_{13}H_{27}O$ | $C_2H_5$ | 1 | para |
| $C_{13}H_{27}O$ | $C_2H_5$ | 1 | meta |
| $C_{13}H_{27}O$ | $C_2H_5$ | 1 | ortho |
| $C_{13}H_{27}O$ | $C_2H_5$ | 2 | ortho/para |
| $C_{14}H_{29}O$ | $C_2H_5$ | 1 | para |
| $C_{14}H_{29}O$ | $C_2H_5$ | 1 | meta |
| $C_{14}H_{29}O$ | $C_2H_5$ | 1 | ortho |
| $C_{14}H_{29}O$ | $C_2H_5$ | 2 | ortho/para |
| $C_{15}H_{31}O$ | $C_2H_5$ | 1 | para |
| $C_{15}H_{31}O$ | $C_2H_5$ | 1 | meta |
| $C_{15}H_{31}O$ | $C_2H_5$ | 1 | ortho |
| $C_{15}H_{31}O$ | $C_2H_5$ | 2 | ortho/para |
| $C_{16}H_{33}O$ | $C_2H_5$ | 1 | para |
| $C_{16}H_{33}O$ | $C_2H_5$ | 1 | meta |
| $C_{16}H_{33}O$ | $C_2H_5$ | 1 | ortho |
| $C_{16}H_{33}O$ | $C_2H_5$ | 2 | ortho/para |
| $C_{17}H_{35}O$ | $C_2H_5$ | 1 | para |
| $C_{17}H_{35}O$ | $C_2H_5$ | 1 | meta |
| $C_{17}H_{35}O$ | $C_2H_5$ | 1 | ortho |
| $C_{17}H_{35}O$ | $C_2H_5$ | 2 | ortho/para |
| $C_{18}H_{37}O$ | $C_2H_5$ | 1 | para |
| $C_{18}H_{37}O$ | $C_2H_5$ | 1 | meta |
| $C_{18}H_{37}O$ | $C_2H_5$ | 1 | ortho |
| $C_{18}H_{37}O$ | $C_2H_5$ | 2 | ortho/para |
| $CH_3O$ | $C_3H_7$ | 1 | meta |
| $CH_3O$ | $C_3H_7$ | 1 | para |
| $CH_3O$ | $C_3H_7$ | 1 | ortho |
| $CH_3O$ | $C_3H_7$ | 2 | ortho/para |
| $C_2H_5O$ | $C_3H_7$ | 1 | para |
| $C_2H_5O$ | $C_3H_7$ | 1 | meta |
| $C_2H_5O$ | $C_3H_7$ | 1 | ortho |
| $C_2H_5O$ | $C_3H_7$ | 2 | ortho/para |
| $C_3H_7O$ | $C_3H_7$ | 1 | para |
| $C_3H_7O$ | $C_3H_7$ | 1 | meta |
| $C_3H_7O$ | $C_3H_7$ | 1 | ortho |
| $C_3H_7O$ | $C_3H_7$ | 2 | ortho/para |
| $C_4H_9O$ | $C_3H_7$ | 1 | para |
| $C_4H_9O$ | $C_3H_7$ | 1 | meta |
| $C_4H_9O$ | $C_3H_7$ | 1 | ortho |
| $C_4H_9O$ | $C_3H_7$ | 2 | ortho/para |
| $C_5H_{11}O$ | $C_3H_7$ | 1 | para |
| $C_5H_{11}O$ | $C_3H_7$ | 1 | meta |
| $C_5H_{11}O$ | $C_3H_7$ | 1 | ortho |
| $C_5H_{11}O$ | $C_3H_7$ | 2 | ortho/para |
| $C_6H_{13}O$ | $C_3H_7$ | 1 | para |
| $C_6H_{13}O$ | $C_3H_7$ | 1 | meta |
| $C_6H_{13}O$ | $C_3H_7$ | 1 | ortho |
| $C_6H_{13}O$ | $C_3H_7$ | 2 | ortho/para |
| $C_8H_{17}O$ | $C_3H_7$ | 1 | para |
| $C_8H_{17}O$ | $C_3H_7$ | 1 | meta |
| $C_8H_{17}O$ | $C_3H_7$ | 1 | ortho |
| $C_8H_{17}O$ | $C_3H_7$ | 2 | ortho/para |
| $C_{12}H_{25}O$ | $C_3H_7$ | 1 | para |
| $C_{12}H_{25}O$ | $C_3H_7$ | 1 | meta |
| $C_{12}H_{25}O$ | $C_3H_7$ | 1 | ortho |
| $C_{12}H_{25}O$ | $C_3H_7$ | 2 | ortho/para |
| $C_{13}H_{27}O$ | $C_3H_7$ | 1 | para |
| $C_{13}H_{27}O$ | $C_3H_7$ | 1 | meta |
| $C_{13}H_{27}O$ | $C_3H_7$ | 1 | ortho |
| $C_{13}H_{27}O$ | $C_3H_7$ | 2 | ortho/para |
| $C_{14}H_{29}O$ | $C_3H_7$ | 1 | para |
| $C_{14}H_{29}O$ | $C_3H_7$ | 1 | meta |
| $C_{14}H_{29}O$ | $C_3H_7$ | 1 | ortho |
| $C_{14}H_{29}O$ | $C_3H_7$ | 2 | ortho/para |
| $C_{15}H_{31}O$ | $C_3H_7$ | 1 | para |
| $C_{15}H_{31}O$ | $C_3H_7$ | 1 | meta |
| $C_{15}H_{31}O$ | $C_3H_7$ | 1 | ortho |
| $C_{15}H_{31}O$ | $C_3H_7$ | 2 | ortho/para |
| $C_{16}H_{33}O$ | $C_3H_7$ | 1 | para |
| $C_{16}H_{33}O$ | $C_3H_7$ | 1 | meta |
| $C_{16}H_{33}O$ | $C_3H_7$ | 1 | ortho |
| $C_{16}H_{33}O$ | $C_3H_7$ | 2 | ortho/para |
| $C_{17}H_{35}O$ | $C_3H_7$ | 1 | para |
| $C_{17}H_{35}O$ | $C_3H_7$ | 1 | meta |
| $C_{17}H_{35}O$ | $C_3H_7$ | 1 | ortho |
| $C_{17}H_{35}O$ | $C_3H_7$ | 2 | ortho/para |
| $C_{18}H_{37}O$ | $C_3H_7$ | 1 | para |
| $C_{18}H_{37}O$ | $C_3H_7$ | 1 | meta |
| $C_{18}H_{37}O$ | $C_3H_7$ | 1 | ortho |
| $C_{18}H_{17}O$ | $C_3H_7$ | 2 | ortho/para |
| $CH_3O$ | $C_4H_9$ | 1 | meta |
| $CH_3O$ | $C_4H_9$ | 1 | para |
| $CH_3O$ | $C_4H_9$ | 1 | ortho |

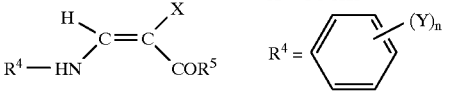

TABLE 1-continued

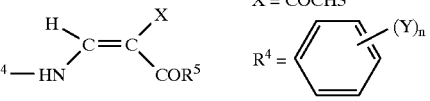

X = COCH3

| Y | R⁵ | n | Position |
|---|---|---|---|
| CH₃O | C₄H₉ | 2 | ortho/para |
| C₂H₅O | C₄H₉ | 1 | para |
| C₂H₅O | C₄H₉ | 1 | meta |
| C₂H₅O | C₄H₉ | 1 | ortho |
| C₂H₅O | C₄H₉ | 2 | ortho/para |
| C₃H₇O | C₄H₉ | 1 | para |
| C₃H₇O | C₄H₉ | 1 | meta |
| C₃H₇O | C₄H₉ | 1 | ortho |
| C₃H₇O | C₄H₉ | 2 | ortho/para |
| C₄H₉O | C₄H₉ | 1 | para |
| C₄H₉O | C₄H₉ | 1 | meta |
| C₄H₉O | C₄H₉ | 1 | ortho |
| C₄H₉O | C₄H₉ | 2 | ortho/para |
| C₅H₁₁O | C₄H₉ | 1 | para |
| C₅H₁₁O | C₄H₉ | 1 | meta |
| C₅H₁₁O | C₄H₉ | 1 | ortho |
| C₅H₁₁O | C₄H₉ | 2 | ortho/para |
| C₆H₁₃O | C₄H₉ | 1 | para |
| C₆H₁₃O | C₄H₉ | 1 | meta |
| C₆H₁₃O | C₄H₉ | 1 | ortho |
| C₆H₁₃O | C₄H₉ | 2 | ortho/para |
| C₈H₁₇O | C₄H₉ | 1 | para |
| C₈H₁₇O | C₄H₉ | 1 | meta |
| C₈H₁₇O | C₄H₉ | 1 | ortho |
| C₈H₁₇O | C₄H₉ | 2 | ortho/para |
| C₁₂H₂₅O | C₄H₉ | 1 | para |
| C₁₂H₂₅O | C₄H₉ | 1 | meta |
| C₁₂H₂₅O | C₄H₉ | 1 | ortho |
| C₁₂H₂₅O | C₄H₉ | 2 | ortho/para |
| C₁₃H₂₇O | C₄H₉ | 1 | para |
| C₁₃H₂₇O | C₄H₉ | 1 | meta |
| C₁₃H₂₇O | C₄H₉ | 1 | ortho |
| C₁₃H₂₇O | C₄H₉ | 2 | ortho/para |
| C₁₄H₂₉O | C₄H₉ | 1 | para |
| C₁₄H₂₉O | C₄H₉ | 1 | meta |
| C₁₄H₂₉O | C₄H₉ | 1 | ortho |
| C₁₄H₂₉O | C₄H₉ | 2 | ortho/para |
| C₁₅H₃₁O | C₄H₉ | 1 | para |
| C₁₅H₃₁O | C₄H₉ | 1 | meta |
| C₁₅H₃₁O | C₄H₉ | 1 | ortho |
| C₁₅H₃₁O | C₄H₉ | 2 | ortho/para |
| C₁₆H₃₃O | C₄H₉ | 1 | para |
| C₁₆H₃₃O | C₄H₉ | 1 | meta |
| C₁₆H₃₃O | C₄H₉ | 1 | ortho |
| C₁₆H₃₃O | C₄H₉ | 2 | ortho/para |
| C₁₇H₃₅O | C₄H₉ | 1 | para |
| C₁₇H₃₅O | C₄H₉ | 1 | meta |
| C₁₇H₃₅O | C₄H₉ | 1 | ortho |
| C₁₇H₃₅O | C₄H₉ | 2 | ortho/para |
| C₁₈H₃₇O | C₄H₉ | 1 | para |
| C₁₈H₃₇O | C₄H₉ | 1 | meta |
| C₁₈H₃₇O | C₄H₉ | 1 | ortho |
| C₁₈H₃₇O | C₄H₉ | 2 | ortho/para |
| CH₃O | C₅H₁₁ | 1 | meta |
| CH₃O | C₅H₁₁ | 1 | para |
| CH₃O | C₅H₁₁ | 1 | ortho |
| CH₃O | C₅H₁₁ | 2 | ortho/para |
| C₂H₅O | C₅H₁₁ | 1 | para |
| C₂H₅O | C₅H₁₁ | 1 | meta |
| C₂H₅O | C₅H₁₁ | 1 | ortho |
| C₂H₅O | C₅H₁₁ | 2 | ortho/para |
| C₃H₇O | C₅H₁₁ | 1 | para |
| C₃H₇O | C₅H₁₁ | 1 | meta |
| C₃H₇O | C₅H₁₁ | 1 | ortho |
| C₃H₇O | C₅H₁₁ | 2 | ortho/para |
| C₄H₉O | C₅H₁₁ | 1 | para |
| C₄H₉O | C₅H₁₁ | 1 | meta |
| C₄H₉O | C₅H₁₁ | 1 | ortho |
| C₄H₉O | C₅H₁₁ | 2 | ortho/para |
| C₅H₁₁O | C₅H₁₁ | 1 | para |

TABLE 1-continued

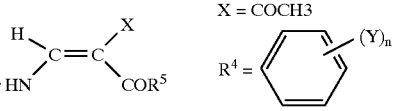

X = COCH3

| Y | R⁵ | n | Position |
|---|---|---|---|
| C₅H₁₁O | C₅H₁₁ | 1 | meta |
| C₅H₁₁O | C₅H₁₁ | 1 | ortho |
| C₅H₁₁O | C₅H₁₁ | 2 | ortho/para |
| C₆H₁₃O | C₅H₁₁ | 1 | para |
| C₆H₁₃O | C₅H₁₁ | 1 | meta |
| C₆H₁₃O | C₅H₁₁ | 1 | ortho |
| C₆H₁₃O | C₅H₁₁ | 2 | ortho/para |
| C₈H₁₇O | C₅H₁₁ | 1 | para |
| C₈H₁₇O | C₅H₁₁ | 1 | meta |
| C₈H₁₇O | C₅H₁₁ | 1 | ortho |
| C₈H₁₇O | C₅H₁₁ | 2 | ortho/para |
| C₁₂H₂₅O | C₅H₁₁ | 1 | para |
| C₁₂H₂₅O | C₅H₁₁ | 1 | meta |
| C₁₂H₂₅O | C₅H₁₁ | 1 | ortho |
| C₁₂H₂₅O | C₅H₁₁ | 2 | ortho/para |
| C₁₃H₂₇O | C₅H₁₁ | 1 | para |
| C₁₃H₂₇O | C₅H₁₁ | 1 | meta |
| C₁₃H₂₇O | C₅H₁₁ | 1 | ortho |
| C₁₃H₂₇O | C₅H₁₁ | 2 | ortho/para |
| C₁₄H₂₉O | C₅H₁₁ | 1 | para |
| C₁₄H₂₉O | C₅H₁₁ | 1 | meta |
| C₁₄H₂₉O | C₅H₁₁ | 1 | ortho |
| C₁₄H₂₉O | C₅H₁₁ | 2 | ortho/para |
| C₁₅H₃₁O | C₅H₁₁ | 1 | para |
| C₁₅H₃₁O | C₅H₁₁ | 1 | meta |
| C₁₅H₃₁O | C₅H₁₁ | 1 | ortho |
| C₁₅H₃₁O | C₅H₁₁ | 2 | ortho/para |
| C₁₆H₃₃O | C₅H₁₁ | 1 | para |
| C₁₆H₃₃O | C₅H₁₁ | 1 | meta |
| C₁₆H₃₃O | C₅H₁₁ | 1 | ortho |
| C₁₆H₃₃O | C₅H₁₁ | 2 | ortho/para |
| C₁₇H₃₅O | C₅H₁₁ | 1 | para |
| C₁₇H₃₅O | C₅H₁₁ | 1 | meta |
| C₁₇H₃₅O | C₅H₁₁ | 1 | ortho |
| C₁₇H₃₅O | C₅H₁₁ | 2 | ortho/para |
| C₁₈H₃₇O | C₅H₁₁ | 1 | para |
| C₁₈H₁₇O | C₅H₁₁ | 1 | meta |
| C₁₈H₃₇O | C₅H₁₁ | 1 | ortho |
| C₁₈H₃₇O | C₅H₁₁ | 2 | ortho/para |
| CH₃O | C₆H₁₃ | 1 | para |
| CH₃O | C₆H₁₃ | 1 | para |
| CH₃O | C₆H₁₃ | 1 | ortho |
| CH₃O | C₆H₁₃ | 2 | ortho/para |
| C₂H₅O | C₆H₁₃ | 1 | para |
| C₂H₅O | C₆H₁₃ | 1 | meta |
| C₂H₅O | C₆H₁₃ | 1 | ortho |
| C₂H₅O | C₆H₁₃ | 2 | ortho/para |
| C₃H₇O | C₆H₁₃ | 1 | para |
| C₃H₇O | C₆H₁₃ | 1 | meta |
| C₃H₇O | C₆H₁₃ | 1 | ortho |
| C₃H₇O | C₆H₁₃ | 2 | ortho/para |
| C₄H₉O | C₆H₁₃ | 1 | para |
| C₄H₉O | C₆H₁₃ | 1 | meta |
| C₄H₉O | C₆H₁₃ | 1 | ortho |
| C₄H₉O | C₆H₁₃ | 2 | ortho/para |
| C₅H₁₁O | C₆H₁₃ | 1 | para |
| C₅H₁₁O | C₆H₁₃ | 1 | meta |
| C₅H₁₁O | C₆H₁₃ | 1 | ortho |
| C₅H₁₁O | C₆H₁₃ | 2 | ortho/para |
| C₆H₁₃O | C₆H₁₃ | 1 | para |
| C₆H₁₃O | C₆H₁₃ | 1 | meta |
| C₆H₁₃O | C₆H₁₃ | 1 | ortho |
| C₆H₁₃O | C₆H₁₃ | 2 | ortho/para |
| C₈H₁₇O | C₆H₁₃ | 1 | para |
| C₈H₁₇O | C₆H₁₃ | 1 | meta |
| C₈H₁₇O | C₆H₁₃ | 1 | ortho |
| C₈H₁₇O | C₆H₁₃ | 2 | ortho/para |
| C₁₂H₂₅O | C₆H₁₃ | 1 | para |
| C₁₂H₂₅O | C₆H₁₃ | 1 | meta |
| C₁₂H₂₅O | C₆H₁₃ | 1 | ortho |

TABLE 1-continued

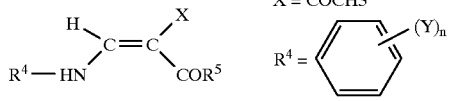

X = COCH3

| Y | R⁵ | n | Position |
|---|---|---|---|
| $C_{12}H_{25}O$ | $C_6H_{13}$ | 2 | ortho/para |
| $C_{13}H_{27}O$ | $C_6H_{13}$ | 1 | para |
| $C_{13}H_{27}O$ | $C_6H_{13}$ | 1 | meta |
| $C_{13}H_{27}O$ | $C_6H_{13}$ | 1 | ortho |
| $C_{13}H_{27}O$ | $C_6H_{13}$ | 2 | ortho/para |
| $C_{14}H_{29}O$ | $C_6H_{13}$ | 1 | para |
| $C_{14}H_{29}O$ | $C_6H_{13}$ | 1 | meta |
| $C_{14}H_{29}O$ | $C_6H_{13}$ | 1 | ortho |
| $C_{14}H_{29}O$ | $C_6H_{13}$ | 2 | ortho/para |
| $C_{15}H_{31}O$ | $C_6H_{13}$ | 1 | para |
| $C_{15}H_{31}O$ | $C_6H_{13}$ | 1 | meta |
| $C_{15}H_{31}O$ | $C_6H_{13}$ | 1 | ortho |
| $C_{15}H_{31}O$ | $C_6H_{13}$ | 2 | ortho/para |
| $C_{16}H_{33}O$ | $C_6H_{13}$ | 1 | para |
| $C_{16}H_{33}O$ | $C_6H_{13}$ | 1 | meta |
| $C_{16}H_{33}O$ | $C_6H_{13}$ | 1 | ortho |
| $C_{16}H_{33}O$ | $C_6H_{13}$ | 2 | ortho/para |
| $C_{17}H_{35}O$ | $C_6H_{13}$ | 1 | para |
| $C_{17}H_{35}O$ | $C_6H_{13}$ | 1 | meta |
| $C_{17}H_{35}O$ | $C_6H_{13}$ | 1 | ortho |
| $C_{17}H_{35}O$ | $C_6H_{13}$ | 2 | ortho/para |
| $C_{18}H_{17}O$ | $C_6H_{13}$ | 1 | para |
| $C_{18}H_{37}O$ | $C_6H_{13}$ | 1 | meta |
| $C_{18}H_{37}O$ | $C_6H_{13}$ | 1 | ortho |
| $C_{18}H_{37}O$ | $C_6H_{13}$ | 2 | ortho/para |
| $CH_3O$ | $CH_3O$ | 1 | meta |
| $CH_3O$ | $CH_3O$ | 1 | para |
| $CH_3O$ | $CH_3O$ | 1 | ortho |
| $CH_3O$ | $CH_3O$ | 2 | ortho/para |
| $C_2H_5O$ | $CH_3O$ | 1 | para |
| $C_2H_5O$ | $CH_3O$ | 1 | meta |
| $C_2H_5O$ | $CH_3O$ | 1 | ortho |
| $C_2H_5O$ | $CH_3O$ | 2 | ortho/para |
| $C_3H_7O$ | $CH_3O$ | 1 | para |
| $C_3H_7O$ | $CH_3O$ | 1 | meta |
| $C_3H_7O$ | $CH_3O$ | 1 | ortho |
| $C_3H_7O$ | $CH_3O$ | 2 | ortho/para |
| $C_4H_9O$ | $CH_3O$ | 1 | para |
| $C_4H_9O$ | $CH_3O$ | 1 | meta |
| $C_4H_9O$ | $CH_3O$ | 1 | ortho |
| $C_4H_9O$ | $CH_3O$ | 2 | ortho/para |
| $C_5H_{11}O$ | $CH_3O$ | 1 | para |
| $C_5H_{11}O$ | $CH_3O$ | 1 | meta |
| $C_5H_{11}O$ | $CH_3O$ | 1 | ortho |
| $C_5H_{11}O$ | $CH_3O$ | 2 | ortho/para |
| $C_6H_{13}O$ | $CH_3O$ | 1 | para |
| $C_6H_{13}O$ | $CH_3O$ | 1 | meta |
| $C_6H_{13}O$ | $CH_3O$ | 1 | ortho |
| $C_6H_{13}O$ | $CH_3O$ | 2 | ortho/para |
| $C_8H_{17}O$ | $CH_3O$ | 1 | para |
| $C_8H_{17}O$ | $CH_3O$ | 1 | meta |
| $C_8H_{17}O$ | $CH_3O$ | 1 | ortho |
| $C_8H_{17}O$ | $CH_3O$ | 2 | ortho/para |
| $C_{12}H_{25}O$ | $CH_3O$ | 1 | para |
| $C_{12}H_{25}O$ | $CH_3O$ | 1 | meta |
| $C_{12}H_{25}O$ | $CH_3O$ | 1 | ortho |
| $C_{12}H_{25}O$ | $CH_3O$ | 2 | ortho/para |
| $C_{13}H_{27}O$ | $CH_3O$ | 1 | para |
| $C_{13}H_{27}O$ | $CH_3O$ | 1 | meta |
| $C_{13}H_{27}O$ | $CH_3O$ | 1 | ortho |
| $C_{13}H_{27}O$ | $CH_3O$ | 2 | ortho/para |
| $C_{14}H_{29}O$ | $CH_3O$ | 1 | para |
| $C_{14}H_{29}O$ | $CH_3O$ | 1 | meta |
| $C_{14}H_{29}O$ | $CH_3O$ | 1 | ortho |
| $C_{14}H_{29}O$ | $CH_3O$ | 2 | ortho/para |
| $C_{15}H_{31}O$ | $CH_3O$ | 1 | para |
| $C_{15}H_{31}O$ | $CH_3O$ | 1 | meta |
| $C_{15}H_{31}O$ | $CH_3O$ | 1 | ortho |
| $C_{15}H_{31}O$ | $CH_3O$ | 2 | ortho/para |
| $C_{16}H_{33}O$ | $CH_3O$ | 1 | para |

TABLE 1-continued

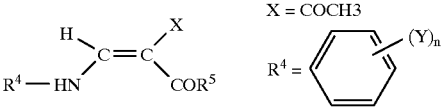

X = COCH3

| Y | R⁵ | n | Position |
|---|---|---|---|
| $C_{16}H_{33}O$ | $CH_3O$ | 1 | meta |
| $C_{16}H_{33}O$ | $CH_3O$ | 1 | ortho |
| $C_{16}H_{33}O$ | $CH_3O$ | 2 | ortho/para |
| $C_{17}H_{35}O$ | $CH_3O$ | 1 | para |
| $C_{17}H_{35}O$ | $CH_3O$ | 1 | meta |
| $C_{17}H_{35}O$ | $CH_3O$ | 1 | ortho |
| $C_{17}H_{35}O$ | $CH_3O$ | 2 | ortho/para |
| $C_{18}H_{37}O$ | $CH_3O$ | 1 | para |
| $C_{18}H_{37}O$ | $CH_3O$ | 1 | meta |
| $C_{18}H_{17}O$ | $CH_3O$ | 1 | ortho |
| $C_{18}H_{37}O$ | $CH_3O$ | 2 | ortho/para |
| $CH_3O$ | $C_2H_5O$ | 1 | para |
| $CH_3O$ | $C_2H_5O$ | 1 | meta |
| $CH_3O$ | $C_2H_5O$ | 1 | ortho |
| $CH_3O$ | $C_2H_5O$ | 2 | ortho/para |
| $C_2H_5O$ | $C_2H_5O$ | 1 | para |
| $C_2H_5O$ | $C_2H_5O$ | 1 | meta |
| $C_2H_5O$ | $C_2H_5O$ | 1 | ortho |
| $C_2H_5O$ | $C_2H_5O$ | 2 | ortho/para |
| $C_3H_7O$ | $C_2H_5O$ | 1 | para |
| $C_3H_7O$ | $C_2H_5O$ | 1 | meta |
| $C_3H_7O$ | $C_2H_5O$ | 1 | ortho |
| $C_3H_7O$ | $C_2H_5O$ | 2 | ortho/para |
| $C_4H_9O$ | $C_2H_5O$ | 1 | para |
| $C_4H_9O$ | $C_2H_5O$ | 1 | meta |
| $C_4H_9O$ | $C_2H_5O$ | 1 | ortho |
| $C_4H_9O$ | $C_2H_5O$ | 2 | ortho/para |
| $C_5H_{11}O$ | $C_2H_5O$ | 1 | para |
| $C_5H_{11}O$ | $C_2H_5O$ | 1 | meta |
| $C_5H_{11}O$ | $C_2H_5O$ | 1 | ortho |
| $C_5H_{11}O$ | $C_2H_5O$ | 2 | ortho/para |
| $C_6H_{13}O$ | $C_2H_5O$ | 1 | para |
| $C_6H_{13}O$ | $C_2H_5O$ | 1 | meta |
| $C_6H_{13}O$ | $C_2H_5O$ | 1 | ortho |
| $C_6H_{13}O$ | $C_2H_5O$ | 2 | ortho/para |
| $C_8H_{17}O$ | $C_2H_5O$ | 1 | para |
| $C_8H_{17}O$ | $C_2H_5O$ | 1 | meta |
| $C_8H_{17}O$ | $C_2H_5O$ | 1 | ortho |
| $C_8H_{17}O$ | $C_2H_5O$ | 2 | ortho/para |
| $C_{12}H_{25}O$ | $C_2H_5O$ | 1 | para |
| $C_{12}H_{25}O$ | $C_2H_5O$ | 1 | meta |
| $C_{12}H_{25}O$ | $C_2H_5O$ | 2 | ortho/para |
| $C_{13}H_{27}O$ | $C_2H_5O$ | 1 | para |
| $C_{13}H_{27}O$ | $C_2H_5O$ | 1 | meta |
| $C_{13}H_{27}O$ | $C_2H_5O$ | 1 | ortho |
| $C_{13}H_{27}O$ | $C_2H_5O$ | 2 | ortho/para |
| $C_{14}H_{29}O$ | $C_2H_5O$ | 1 | para |
| $C_{14}H_{29}O$ | $C_2H_5O$ | 1 | meta |
| $C_{14}H_{29}O$ | $C_2H_5O$ | 1 | ortho |
| $C_{14}H_{29}O$ | $C_2H_5O$ | 2 | ortho/para |
| $C_{15}H_{31}O$ | $C_2H_5O$ | 1 | para |
| $C_{15}H_{31}O$ | $C_2H_5O$ | 1 | meta |
| $C_{15}H_{31}O$ | $C_2H_5O$ | 1 | ortho |
| $C_{15}H_{31}O$ | $C_2H_5O$ | 2 | ortho/para |
| $C_{16}H_{33}O$ | $C_2H_5O$ | 1 | para |
| $C_{16}H_{33}O$ | $C_2H_5O$ | 1 | meta |
| $C_{16}H_{33}O$ | $C_2H_5O$ | 1 | ortho |
| $C_{16}H_{33}O$ | $C_2H_5O$ | 2 | ortho/para |
| $C_{17}H_{35}O$ | $C_2H_5O$ | 1 | para |
| $C_{17}H_{35}O$ | $C_2H_5O$ | 1 | meta |
| $C_{17}H_{35}O$ | $C_2H_5O$ | 1 | ortho |
| $C_{17}H_{35}O$ | $C_2H_5O$ | 2 | ortho/para |
| $C_{18}H_{37}O$ | $C_2H_5O$ | 1 | para |
| $C_{18}H_{37}O$ | $C_2H_5O$ | 1 | meta |
| $C_{18}H_{37}O$ | $C_2H_5O$ | 1 | ortho |
| $C_{18}H_{37}O$ | $C_2H_5O$ | 2 | ortho/para |
| $CH_3O$ | $C_3H_7O$ | 1 | para |
| $CH_3O$ | $C_3H_7O$ | 1 | meta |
| $CH_3O$ | $C_3H_7O$ | 1 | ortho |
| $CH_3O$ | $C_3H_7O$ | 2 | ortho/para |

TABLE 1-continued

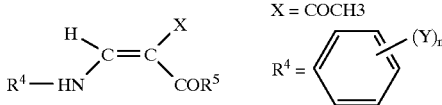
X = COCH3

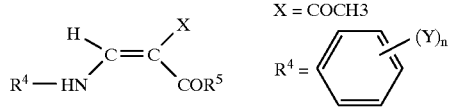

| Y | $R^5$ | n | Position |
|---|---|---|---|
| $C_2H_5O$ | $C_3H_7O$ | 1 | para |
| $C_2H_5O$ | $C_3H_7O$ | 1 | meta |
| $C_2H_5O$ | $C_3H_7O$ | 1 | ortho |
| $C_2H_5O$ | $C_3H_7O$ | 2 | ortho/para |
| $C_3H_7O$ | $C_3H_7O$ | 1 | para |
| $C_3H_7O$ | $C_3H_7O$ | 1 | meta |
| $C_3H_7O$ | $C_3H_7O$ | 1 | ortho |
| $C_3H_7O$ | $C_3H_7O$ | 2 | ortho/para |
| $C_4H_9O$ | $C_3H_7O$ | 1 | para |
| $C_4H_9O$ | $C_3H_7O$ | 1 | meta |
| $C_4H_9O$ | $C_3H_7O$ | 1 | ortho |
| $C_4H_9O$ | $C_3H_7O$ | 2 | ortho/para |
| $C_5H_{11}O$ | $C_3H_7O$ | 1 | para |
| $C_5H_{11}O$ | $C_3H_7O$ | 1 | meta |
| $C_5H_{11}O$ | $C_3H_7O$ | 1 | ortho |
| $C_5H_{11}O$ | $C_3H_7O$ | 2 | ortho/para |
| $C_6H_{13}O$ | $C_3H_7O$ | 1 | para |
| $C_6H_{13}O$ | $C_3H_7O$ | 1 | meta |
| $C_6H_{13}O$ | $C_3H_7O$ | 1 | ortho |
| $C_6H_{13}O$ | $C_3H_7O$ | 2 | ortho/para |
| $C_8H_{17}O$ | $C_3H_7O$ | 1 | para |
| $C_8H_{17}O$ | $C_3H_7O$ | 1 | meta |
| $C_8H_{17}O$ | $C_3H_7O$ | 1 | ortho |
| $C_8H_{17}O$ | $C_3H_7O$ | 2 | ortho/para |
| $C_{12}H_{25}O$ | $C_3H_7O$ | 1 | para |
| $C_{12}H_{25}O$ | $C_3H_7O$ | 1 | meta |
| $C_{12}H_{25}O$ | $C_3H_7O$ | 1 | ortho |
| $C_{12}H_{25}O$ | $C_3H_7O$ | 2 | ortho/para |
| $C_{13}H_{27}O$ | $C_3H_7O$ | 1 | para |
| $C_{13}H_{27}O$ | $C_3H_7O$ | 1 | meta |
| $C_{13}H_{27}O$ | $C_3H_7O$ | 1 | ortho |
| $C_{13}H_{27}O$ | $C_3H_7O$ | 2 | ortho/para |
| $C_{14}H_{29}O$ | $C_3H_7O$ | 1 | para |
| $C_{14}H_{29}O$ | $C_3H_7O$ | 1 | meta |
| $C_{14}H_{29}O$ | $C_3H_7O$ | 1 | ortho |
| $C_{14}H_{29}O$ | $C_3H_7O$ | 2 | ortho/para |
| $C_{15}H_{31}O$ | $C_3H_7O$ | 1 | para |
| $C_{15}H_{31}O$ | $C_3H_7O$ | 1 | meta |
| $C_{15}H_{31}O$ | $C_3H_7O$ | 1 | ortho |
| $C_{15}H_{31}O$ | $C_3H_7O$ | 2 | ortho/para |
| $C_{16}H_{33}O$ | $C_3H_7O$ | 1 | para |
| $C_{16}H_{33}O$ | $C_3H_7O$ | 1 | meta |
| $C_{16}H_{33}O$ | $C_3H_7O$ | 1 | ortho |
| $C_{16}H_{33}O$ | $C_3H_7O$ | 2 | ortho/para |
| $C_{17}H_{35}O$ | $C_3H_7O$ | 1 | para |
| $C_{17}H_{35}O$ | $C_3H_7O$ | 1 | meta |
| $C_{17}H_{35}O$ | $C_3H_7O$ | 1 | ortho |
| $C_{17}H_{35}O$ | $C_3H_7O$ | 2 | ortho/para |
| $C_{18}H_{37}O$ | $C_3H_7O$ | 1 | para |
| $C_{18}H_{37}O$ | $C_3H_7O$ | 1 | meta |
| $C_{18}H_{37}O$ | $C_3H_7O$ | 1 | ortho |
| $C_{18}H_{37}O$ | $C_3H_7O$ | 2 | ortho/para |
| $CH_3O$ | $C_4H_9O$ | 1 | para |
| $CH_3O$ | $C_4H_9O$ | 1 | meta |
| $CH_3O$ | $C_4H_9O$ | 1 | ortho |
| $CH_3O$ | $C_4H_9O$ | 2 | ortho/para |
| $C_2H_5O$ | $C_4H_9O$ | 1 | para |
| $C_2H_5O$ | $C_4H_9O$ | 1 | meta |
| $C_2H_5O$ | $C_4H_9O$ | 1 | ortho |
| $C_2H_5O$ | $C_4H_9O$ | 2 | ortho/para |
| $C_3H_7O$ | $C_4H_9O$ | 1 | para |
| $C_3H_7O$ | $C_4H_9O$ | 1 | meta |
| $C_3H_7O$ | $C_4H_9O$ | 1 | ortho |
| $C_3H_7O$ | $C_4H_9O$ | 2 | ortho/para |
| $C_4H_9O$ | $C_4H_9O$ | 1 | para |
| $C_4H_9O$ | $C_4H_9O$ | 1 | meta |
| $C_4H_9O$ | $C_4H_9O$ | 1 | ortho |
| $C_4H_9O$ | $C_4H_9O$ | 2 | ortho/para |
| $C_5H_{11}O$ | $C_4H_9O$ | 1 | para |
| $C_5H_{11}O$ | $C_4H_9O$ | 1 | meta |
| $C_5H_{11}O$ | $C_4H_9O$ | 1 | ortho |
| $C_5H_{11}O$ | $C_4H_9O$ | 2 | ortho/para |
| $C_6H_{13}O$ | $C_4H_9O$ | 1 | para |
| $C_6H_{13}O$ | $C_4H_9O$ | 1 | meta |
| $C_6H_{13}O$ | $C_4H_9O$ | 1 | ortho |
| $C_6H_{13}O$ | $C_4H_9O$ | 2 | ortho/para |
| $C_8H_{17}O$ | $C_4H_9O$ | 1 | para |
| $C_8H_{17}O$ | $C_4H_9O$ | 1 | meta |
| $C_8H_{17}O$ | $C_4H_9O$ | 1 | ortho |
| $C_8H_{17}O$ | $C_4H_9O$ | 2 | ortho/para |
| $C_{12}H_{25}O$ | $C_4H_9O$ | 1 | para |
| $C_{12}H_{25}O$ | $C_4H_9O$ | 1 | meta |
| $C_{12}H_{25}O$ | $C_4H_9O$ | 1 | ortho |
| $C_{12}H_{25}O$ | $C_4H_9O$ | 2 | ortho/para |
| $C_{13}H_{27}O$ | $C_4H_9O$ | 1 | para |
| $C_{13}H_{27}O$ | $C_4H_9O$ | 1 | meta |
| $C_{13}H_{27}O$ | $C_4H_9O$ | 1 | ortho |
| $C_{13}H_{27}O$ | $C_4H_9O$ | 2 | ortho/para |
| $C_{14}H_{29}O$ | $C_4H_9O$ | 1 | para |
| $C_{14}H_{29}O$ | $C_4H_9O$ | 1 | meta |
| $C_{14}H_{29}O$ | $C_4H_9O$ | 1 | ortho |
| $C_{14}H_{29}O$ | $C_4H_9O$ | 2 | ortho/para |
| $C_{15}H_{31}O$ | $C_4H_9O$ | 1 | para |
| $C_{15}H_{31}O$ | $C_4H_9O$ | 1 | meta |
| $C_{15}H_{31}O$ | $C_4H_9O$ | 1 | ortho |
| $C_{15}H_{31}O$ | $C_4H_9O$ | 2 | ortho/para |
| $C_{16}H_{33}O$ | $C_4H_9O$ | 1 | para |
| $C_{16}H_{33}O$ | $C_4H_9O$ | 1 | meta |
| $C_{16}H_{33}O$ | $C_4H_9O$ | 1 | ortho |
| $C_{16}H_{33}O$ | $C_4H_9O$ | 2 | ortho/para |
| $C_{17}H_{35}O$ | $C_4H_9O$ | 1 | para |
| $C_{17}H_{35}O$ | $C_4H_9O$ | 1 | meta |
| $C_{17}H_{35}O$ | $C_4H_9O$ | 1 | ortho |
| $C_{17}H_{35}O$ | $C_4H_9O$ | 2 | ortho/para |
| $C_{18}H_{37}O$ | $C_4H_9O$ | 1 | para |
| $C_{18}H_{37}O$ | $C_4H_9O$ | 1 | meta |
| $C_{18}H_{37}O$ | $C_4H_9O$ | 1 | ortho |
| $C_{18}H_{37}O$ | $C_4H_9O$ | 2 | ortho/para |
| $CH_3O$ | $C_5H_{11}O$ | 1 | para |
| $CH_3O$ | $C_5H_{11}O$ | 1 | meta |
| $CH_3O$ | $C_5H_{11}O$ | 1 | ortho |
| $CH_3O$ | $C_5H_{11}O$ | 2 | ortho/para |
| $C_2H_5O$ | $C_5H_{11}O$ | 1 | para |
| $C_2H_5O$ | $C_5H_{11}O$ | 1 | meta |
| $C_2H_5O$ | $C_5H_{11}O$ | 1 | ortho |
| $C_2H_5O$ | $C_5H_{11}O$ | 2 | ortho/para |
| $C_3H_7O$ | $C_5H_{11}O$ | 1 | para |
| $C_3H_7O$ | $C_5H_{11}O$ | 1 | meta |
| $C_3H_7O$ | $C_5H_{11}O$ | 1 | ortho |
| $C_3H_7O$ | $C_5H_{11}O$ | 2 | ortho/para |
| $C_4H_9O$ | $C_5H_{11}O$ | 1 | para |
| $C_4H_9O$ | $C_5H_{11}O$ | 1 | meta |
| $C_4H_9O$ | $C_5H_{11}O$ | 1 | ortho |
| $C_4H_9O$ | $C_5H_{11}O$ | 2 | ortho/para |
| $C_5H_{11}O$ | $C_5H_{11}O$ | 1 | para |
| $C_5H_{11}O$ | $C_5H_{11}O$ | 1 | meta |
| $C_5H_{11}O$ | $C_5H_{11}O$ | 1 | ortho |
| $C_5H_{11}O$ | $C_5H_{11}O$ | 2 | ortho/para |
| $C_6H_{13}O$ | $C_5H_{11}O$ | 1 | para |
| $C_6H_{13}O$ | $C_5H_{11}O$ | 1 | meta |
| $C_6H_{13}O$ | $C_5H_{11}O$ | 1 | ortho |
| $C_6H_{13}O$ | $C_5H_{11}O$ | 2 | ortho/para |
| $C_8H_{17}O$ | $C_5H_{11}O$ | 1 | para |
| $C_8H_{17}O$ | $C_5H_{11}O$ | 1 | meta |
| $C_8H_{17}O$ | $C_5H_{11}O$ | 1 | ortho |
| $C_8H_{17}O$ | $C_5H_{11}O$ | 2 | ortho/para |
| $C_{12}H_{25}O$ | $C_5H_{11}O$ | 1 | para |
| $C_{12}H_{25}O$ | $C_5H_{11}O$ | 1 | meta |
| $C_{12}H_{25}O$ | $C_5H_{11}O$ | 1 | ortho |
| $C_{12}H_{25}O$ | $C_5H_{11}O$ | 2 | ortho/para |

TABLE 1-continued

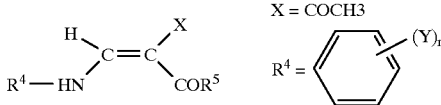

X = COCH3

| Y | R⁵ | n | Position |
|---|---|---|---|
| $C_{13}H_{27}O$ | $C_5H_{11}O$ | 1 | para |
| $C_{13}H_{27}O$ | $C_5H_{11}O$ | 1 | meta |
| $C_{13}H_{27}O$ | $C_5H_{11}O$ | 1 | ortho |
| $C_{13}H_{27}O$ | $C_5H_{11}O$ | 2 | ortho/para |
| $C_{14}H_{29}O$ | $C_5H_{11}O$ | 1 | para |
| $C_{14}H_{29}O$ | $C_5H_{11}O$ | 1 | meta |
| $C_{14}H_{29}O$ | $C_5H_{11}O$ | 1 | ortho |
| $C_{14}H_{29}O$ | $C_5H_{11}O$ | 2 | ortho/para |
| $C_{15}H_{31}O$ | $C_5H_{11}O$ | 1 | para |
| $C_{15}H_{31}O$ | $C_5H_{11}O$ | 1 | meta |
| $C_{15}H_{31}O$ | $C_5H_{11}O$ | 1 | ortho |
| $C_{15}H_{31}O$ | $C_5H_{11}O$ | 2 | ortho/para |
| $C_{16}H_{33}O$ | $C_5H_{11}O$ | 1 | para |
| $C_{16}H_{33}O$ | $C_5H_{11}O$ | 1 | meta |
| $C_{16}H_{33}O$ | $C_5H_{11}O$ | 1 | ortho |
| $C_{16}H_{33}O$ | $C_5H_{11}O$ | 2 | ortho/para |
| $C_{17}H_{35}O$ | $C_5H_{11}O$ | 1 | para |
| $C_{17}H_{35}O$ | $C_5H_{11}O$ | 1 | meta |
| $C_{17}H_{35}O$ | $C_5H_{11}O$ | 1 | ortho |
| $C_{17}H_{35}O$ | $C_5H_{11}O$ | 2 | ortho/para |
| $C_{18}H_{37}O$ | $C_5H_{11}O$ | 1 | para |
| $C_{18}H_{37}O$ | $C_5H_{119}$ | 1 | meta |
| $C_{18}H_{37}O$ | $C_5H_{11}O$ | 1 | ortho |
| $C_{18}H_{17}O$ | $C_5H_{11}O$ | 2 | ortho/para |
| $CH_3O$ | $C_6H_{13}O$ | 1 | para |
| $CH_3O$ | $C_6H_{13}O$ | 1 | meta |
| $CH_3O$ | $C_6H_{13}O$ | 1 | ortho |
| $CH_3O$ | $C_6H_{13}O$ | 2 | ortho/para |
| $C_2H_5O$ | $C_6H_{13}O$ | 1 | para |
| $C_2H_5O$ | $C_6H_{13}O$ | 1 | meta |
| $C_2H_5O$ | $C_6H_{13}O$ | 1 | ortho |
| $C_2H_5O$ | $C_6H_{13}O$ | 2 | ortho/para |
| $C_3H_7O$ | $C_6H_{13}O$ | 1 | para |
| $C_3H_7O$ | $C_6H_{13}O$ | 1 | meta |
| $C_3H_7O$ | $C_6H_{13}O$ | 1 | ortho |
| $C_3H_7O$ | $C_6H_{13}O$ | 2 | ortho/para |
| $C_4H_9O$ | $C_6H_{13}O$ | 1 | para |
| $C_4H_9O$ | $C_6H_{13}O$ | 1 | meta |
| $C_4H_9O$ | $C_6H_{13}O$ | 1 | ortho |
| $C_4H_9O$ | $C_6H_{13}O$ | 2 | ortho/para |
| $C_5H_{11}O$ | $C_6H_{13}O$ | 1 | para |
| $C_5H_{11}O$ | $C_6H_{13}O$ | 1 | meta |
| $C_5H_{11}O$ | $C_6H_{13}O$ | 1 | ortho |
| $C_5H_{11}O$ | $C_6H_{13}O$ | 2 | ortho/para |
| $C_6H_{13}O$ | $C_6H_{13}O$ | 1 | para |
| $C_6H_{13}O$ | $C_6H_{13}O$ | 1 | meta |
| $C_6H_{13}O$ | $C_6H_{13}O$ | 1 | ortho |
| $C_6H_{13}O$ | $C_6H_{13}O$ | 2 | ortho/para |
| $C_8H_{17}O$ | $C_6H_{13}O$ | 1 | para |
| $C_8H_{17}O$ | $C_6H_{13}O$ | 1 | meta |
| $C_8H_{17}O$ | $C_6H_{13}O$ | 1 | ortho |
| $C_8H_{17}O$ | $C_6H_{13}O$ | 2 | ortho/para |
| $C_{12}H_{25}O$ | $C_6H_{13}O$ | 1 | para |
| $C_{12}H_{25}O$ | $C_6H_{13}O$ | 1 | meta |
| $C_{12}H_{25}O$ | $C_6H_{13}O$ | 1 | ortho |
| $C_{12}H_{25}O$ | $C_6H_{13}O$ | 2 | ortho/para |
| $C_{13}H_{27}O$ | $C_6H_{13}O$ | 1 | para |
| $C_{13}H_{27}O$ | $C_6H_{13}O$ | 1 | meta |
| $C_{13}H_{27}O$ | $C_6H_{13}O$ | 1 | ortho |
| $C_{13}H_{27}O$ | $C_6H_{13}O$ | 2 | ortho/para |
| $C_{14}H_{29}O$ | $C_6H_{13}O$ | 1 | para |
| $C_{14}H_{29}O$ | $C_6H_{13}O$ | 1 | meta |
| $C_{14}H_{29}O$ | $C_6H_{13}O$ | 1 | ortho |
| $C_{14}H_{29}O$ | $C_6H_{13}O$ | 2 | ortho/para |
| $C_{15}H_{31}O$ | $C_6H_{13}O$ | 1 | para |
| $C_{15}H_{31}O$ | $C_6H_{13}O$ | 1 | meta |
| $C_{15}H_{31}O$ | $C_6H_{13}O$ | 1 | ortho |
| $C_{15}H_{31}O$ | $C_6H_{13}O$ | 2 | ortho/para |
| $C_{16}H_{33}O$ | $C_6H_{13}O$ | 1 | para |
| $C_{16}H_{33}O$ | $C_6H_{13}O$ | 1 | meta |
| $C_{16}H_{33}O$ | $C_6H_{13}O$ | 1 | ortho |
| $C_{16}H_{33}O$ | $C_6H_{13}O$ | 2 | ortho/para |
| $C_{17}H_{35}O$ | $C_6H_{13}O$ | 1 | para |
| $C_{17}H_{35}O$ | $C_6H_{13}O$ | 1 | meta |
| $C_{17}H_{35}O$ | $C_6H_{13}O$ | 1 | ortho |
| $C_{17}H_{35}O$ | $C_6H_{13}O$ | 2 | ortho/para |
| $C_{18}H_{37}O$ | $C_6H_{13}O$ | 1 | para |
| $C_{18}H_{37}O$ | $C_6H_{13}O$ | 1 | meta |
| $C_{18}H_{37}O$ | $C_6H_{13}O$ | 1 | ortho |
| $C_{18}H_{37}O$ | $C_6H_{13}O$ | 2 | ortho/para |
| $CH_3O$ | $C_7H_{15}O$ | 1 | para |
| $CH_3O$ | $C_7H_{15}O$ | 1 | meta |
| $CH_3O$ | $C_7H_{15}O$ | 1 | ortho |
| $CH_3O$ | $C_7H_{15}O$ | 2 | ortho/para |
| $C_2H_5O$ | $C_7H_{15}O$ | 1 | para |
| $C_2H_5O$ | $C_7H_{15}O$ | 1 | meta |
| $C_2H_5O$ | $C_7H_{15}O$ | 1 | ortho |
| $C_2H_5O$ | $C_7H_{15}O$ | 2 | ortho/para |
| $C_3H_7O$ | $C_7H_{15}O$ | 1 | para |
| $C_3H_7O$ | $C_7H_{15}O$ | 1 | meta |
| $C_3H_7O$ | $C_7H_{15}O$ | 1 | ortho |
| $C_3H_7O$ | $C_7H_{15}O$ | 2 | ortho/para |
| $C_4H_9O$ | $C_7H_{15}O$ | 1 | para |
| $C_4H_9O$ | $C_7H_{15}O$ | 1 | meta |
| $C_4H_9O$ | $C_7H_{15}O$ | 1 | ortho |
| $C_4H_9O$ | $C_7H_{15}O$ | 2 | ortho/para |
| $C_5H_{11}O$ | $C_7H_{15}O$ | 1 | para |
| $C_5H_{11}O$ | $C_7H_{15}O$ | 1 | meta |
| $C_5H_{11}O$ | $C_7H_{15}O$ | 1 | ortho |
| $C_5H_{11}O$ | $C_7H_{15}O$ | 2 | ortho/para |
| $C_6H_{13}O$ | $C_7H_{15}O$ | 1 | para |
| $C_6H_{13}O$ | $C_7H_{15}O$ | 1 | meta |
| $C_6H_{13}O$ | $C_7H_{15}O$ | 1 | ortho |
| $C_6H_{13}O$ | $C_7H_{15}O$ | 2 | ortho/para |
| $C_8H_{17}O$ | $C_7H_{15}O$ | 1 | para |
| $C_8H_{17}O$ | $C_7H_{15}O$ | 1 | meta |
| $C_8H_{17}O$ | $C_7H_{15}O$ | 1 | ortho |
| $C_8H_{17}O$ | $C_7H_{15}O$ | 2 | ortho/para |
| $C_{12}H_{25}O$ | $C_7H_{15}O$ | 1 | para |
| $C_{12}H_{25}O$ | $C_7H_{15}O$ | 1 | meta |
| $C_{12}H_{25}O$ | $C_7H_{15}O$ | 1 | ortho |
| $C_{12}H_{25}O$ | $C_7H_{15}O$ | 2 | ortho/para |
| $C_{13}H_{27}O$ | $C_7H_{15}O$ | 1 | para |
| $C_{13}H_{27}O$ | $C_7H_{15}O$ | 1 | meta |
| $C_{13}H_{27}O$ | $C_7H_{15}O$ | 1 | ortho |
| $C_{13}H_{27}O$ | $C_7H_{15}O$ | 2 | ortho/para |
| $C_{14}H_{29}O$ | $C_7H_{15}O$ | 1 | para |
| $C_{14}H_{29}O$ | $C_7H_{15}O$ | 1 | meta |
| $C_{14}H_{29}O$ | $C_7H_{15}O$ | 1 | ortho |
| $C_{14}H_{29}O$ | $C_7H_{15}O$ | 2 | ortho/para |
| $C_{15}H_{31}O$ | $C_7H_{15}O$ | 1 | para |
| $C_{15}H_{31}O$ | $C_7H_{15}O$ | 1 | meta |
| $C_{15}H_{31}O$ | $C_7H_{15}O$ | 1 | ortho |
| $C_{15}H_{31}O$ | $C_7H_{15}O$ | 2 | ortho/para |
| $C_{16}H_{33}O$ | $C_7H_{15}O$ | 1 | para |
| $C_{16}H_{33}O$ | $C_7H_{15}O$ | 1 | meta |
| $C_{16}H_{33}O$ | $C_7H_{15}O$ | 1 | ortho |
| $C_{16}H_{33}O$ | $C_7H_{15}O$ | 2 | ortho/para |
| $C_{17}H_{35}O$ | $C_7H_{15}O$ | 1 | para |
| $C_{17}H_{35}O$ | $C_7H_{15}O$ | 1 | meta |
| $C_{17}H_{35}O$ | $C_7H_{15}O$ | 1 | ortho |
| $C_{17}H_{35}O$ | $C_7H_{15}O$ | 2 | ortho/para |
| $C_{18}H_{37}O$ | $C_7H_{15}O$ | 1 | para |
| $C_{18}H_{37}O$ | $C_7H_{15}O$ | 1 | meta |
| $C_{18}H_{37}O$ | $C_7H_{15}O$ | 1 | ortho |
| $C_{18}H_{37}O$ | $C_7H_{15}O$ | 2 | ortho/para |
| $CH_3O$ | $C_8H_{17}O$ | 1 | para |
| $CH_3O$ | $C_8H_{17}O$ | 1 | meta |
| $CH_3O$ | $C_8H_{17}O$ | 1 | ortho |
| $CH_3O$ | $C_8H_{17}O$ | 2 | ortho/para |

TABLE 1-continued $$\underset{R^4-HN}{\overset{H}{\diagdown}}C=C\underset{COR^5}{\overset{X}{\diagup}} \quad \begin{array}{l} X = COCH3 \\ R^4 = \end{array} \underset{}{\diagup\!\!\!\diagdown}(Y)_n$$

| Y | $R^5$ | n | Position |
|---|---|---|---|
| $C_2H_5O$ | $C_8H_{17}O$ | 1 | para |
| $C_2H_5O$ | $C_8H_{17}O$ | 1 | meta |
| $C_2H_5O$ | $C_8H_{17}O$ | 1 | ortho |
| $C_2H_5O$ | $C_8H_{17}O$ | 2 | ortho/para |
| $C_3H_7O$ | $C_8H_{17}O$ | 1 | para |
| $C_3H_7O$ | $C_8H_{17}O$ | 1 | meta |
| $C_3H_7O$ | $C_8H_{17}O$ | 1 | ortho |
| $C_3H_7O$ | $C_8H_{17}O$ | 2 | ortho/para |
| $C_4H_9O$ | $C_8H_{17}O$ | 1 | para |
| $C_4H_9O$ | $C_8H_{17}O$ | 1 | meta |
| $C_4H_9O$ | $C_8H_{17}O$ | 1 | ortho |
| $C_4H_9O$ | $C_8H_{17}O$ | 2 | ortho/para |
| $C_5H_{11}O$ | $C_8H_{17}O$ | 1 | para |
| $C_5H_{11}O$ | $C_8H_{17}O$ | 1 | meta |
| $C_5H_{11}O$ | $C_8H_{17}O$ | 1 | ortho |
| $C_5H_{11}O$ | $C_8H_{17}O$ | 2 | ortho/para |
| $C_6H_{13}O$ | $C_8H_{17}O$ | 1 | para |
| $C_6H_{13}O$ | $C_8H_{17}O$ | 1 | meta |
| $C_6H_{13}O$ | $C_8H_{17}O$ | 1 | ortho |
| $C_6H_{13}O$ | $C_8H_{17}O$ | 2 | ortho/para |
| $C_8H_{17}O$ | $C_8H_{17}O$ | 1 | para |
| $C_8H_{17}O$ | $C_8H_{17}O$ | 1 | meta |
| $C_8H_{17}O$ | $C_8H_{17}O$ | 1 | ortho |
| $C_8H_{17}O$ | $C_8H_{17}O$ | 2 | ortho/para |
| $C_{12}H_{25}O$ | $C_8H_{17}O$ | 1 | para |
| $C_{12}H_{25}O$ | $C_8H_{17}O$ | 1 | meta |
| $C_{12}H_{25}O$ | $C_8H_{17}O$ | 1 | ortho |
| $C_{12}H_{25}O$ | $C_8H_{17}O$ | 2 | ortho/para |
| $C_{13}H_{27}O$ | $C_8H_{17}O$ | 1 | para |
| $C_{13}H_{27}O$ | $C_8H_{17}O$ | 1 | meta |
| $C_{13}H_{27}O$ | $C_8H_{17}O$ | 1 | ortho |
| $C_{13}H_{27}O$ | $C_8H_{17}O$ | 2 | ortho/para |
| $C_{14}H_{29}O$ | $C_8H_{17}O$ | 1 | para |
| $C_{14}H_{29}O$ | $C_8H_{17}O$ | 1 | meta |
| $C_{14}H_{29}O$ | $C_8H_{17}O$ | 1 | ortho |
| $C_{14}H_{29}O$ | $C_8H_{17}O$ | 2 | ortho/para |
| $C_{15}H_{31}O$ | $C_8H_{17}O$ | 1 | para |
| $C_{15}H_{31}O$ | $C_8H_{17}O$ | 1 | meta |
| $C_{15}H_{31}O$ | $C_8H_{17}O$ | 1 | ortho |
| $C_{15}H_{31}O$ | $C_8H_{17}O$ | 2 | ortho/para |
| $C_{16}H_{33}O$ | $C_8H_{17}O$ | 1 | para |
| $C_{16}H_{33}O$ | $C_8H_{17}O$ | 1 | meta |
| $C_{16}H_{33}O$ | $C_8H_{17}O$ | 1 | ortho |
| $C_{16}H_{33}O$ | $C_8H_{17}O$ | 2 | ortho/para |
| $C_{17}H_{35}O$ | $C_8H_{17}O$ | 1 | para |
| $C_{17}H_{35}O$ | $C_8H_{17}O$ | 1 | meta |
| $C_{17}H_{35}O$ | $C_8H_{17}O$ | 1 | ortho |
| $C_{17}H_{35}O$ | $C_8H_{17}O$ | 2 | ortho/para |
| $C_{18}H_{37}O$ | $C_8H_{17}O$ | 1 | para |
| $C_{18}H_{37}O$ | $C_8H_{17}O$ | 1 | meta |
| $C_{18}H_{37}O$ | $C_8H_{17}O$ | 1 | ortho |
| $C_{18}H_{37}O$ | $C_8H_{17}O$ | 2 | ortho/para |

The compounds of formula I to be used in the present invention may be prepared by condensation according to the following equation:

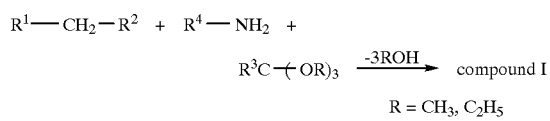

$$R^1-CH_2-R^2 \;+\; R^4-NH_2 \;+\; R^3C\text{---}(OR)_3 \xrightarrow{-3ROH} \text{compound I}$$

$$R = CH_3, C_2H_5$$

in which $R^1$ to $R^4$ have the meanings specified above.

For example, the reaction of 2,4-pentanedione with 2-ethylhexyl anthranilate and triethyl orthoformate gives compound 24 in Table 2.

The cosmetic and pharmaceutical formulations containing screening agents are usually based on a carrier containing at least one oily phase. Alternatively formulations based on water alone are possible when using compounds containing hydrophilic substituents. Accordingly oils, oil-in-water emulsions, water-in-oil emulsions, creams and pastes, protective lipstick compositions or grease-free gels are suitable types of formulation.

Such sun-shading preparations can accordingly exist in liquid, pasty or solid form, for example as water-in-oil creams, oil-in-water creams and lotions, aerosol foaming creams, gels, oils, grease sticks, powders, sprays or aqueous alcoholic lotions.

Common oily components used in the cosmetics industry are for example liquid paraffin, glyceryl stearate, isopropyl myristate, diisopropyl adipate, cetylstaeryl 2-ethylhexanoate, polyisobutene, vaselines, caprylic/capric triglycerides, microcrystalline wax, lanolin and stearic acid.

Common cosmetic auxiliaries which are suitable for use as additives are, for example, co-emulsifiers, greases and waxes, stabilizers, thickeners, biogenetically active substances, film formers, perfumes, dyes, pearl-lustering agents, preservatives, pigments, electrolytes (eg magnesium sulfate) and pH regulators. Suitable co-emulsifiers are preferably known water-in-oil emulsifiers and also oil-in-water emulsifiers such as poly(glycerol ester)s, sorbitan esters or glycerides. Typical examples of greases are glycerides; examples of suitable waxes are, inter alia, beeswax, paraffin wax or microwaxes optionally in combination with hydrophilic waxes. Stabilizers that can be used are, for example, metal salts of fatty acids such as magnesium, aluminum and/or zinc stearate. Suitable thickeners are for example cross-linked poly(acrylic acid)s and their derivatives, polysaccharides, particularly xanthan-gum, guar-guar, agar-agar, alginates and tyloses, carboxylmethylcellusose and hydroxyethylcellulose, also fatty alcohols, monoglycerides and fatty acids, polyacrylates, poly(vinyl alcohol) and poly(vinyl pyrrolidone). By biogenetically active substances we mean, for example, plant extracts, protein hydrolysates and vitamin complexes. Commonly used film formers are for example hydrocolloids such as chitosan, microcrystalline chitosan or quaternized chitosan, poly(vinyl pyrrolidone), poly(vinyl pyrrolidone-co-vinyl acetate)s, polymers of the acrylic acid series, quaternary cellulose derivatives and similar compounds. Suitable preservatives are for example formaldehyde solution, p-hydroxybenzoate or sorbic acid. Suitable pearl-lustering agents are for example glycol distearates such as ethylene glycol distearate, and also fatty acids and fatty acid monoglycol esters. The dyestuffs used may be any of the substances which are suitable and licensed for cosmetic purposes, as listed, for example, in "Kosmetische Färbemittel" issued by the Farbstoffkommission der Deutschen Forschungsgemeinschaft and published by Verlag Chemie, Weinheim, 1984. These dyestuffs can be used in concentrations usually ranging from 0.001 to 0.1 wt %, based on the total mixture. The total concentration of the auxiliaries and additives can be from 1 to 80 and preferably from 6 to 40wt% and the non-aqueous content ("active substance") may be from 20 to 80 and preferably from 30 to 70 wt %—based on the agents used. The preparation of the agents can be carried out in known manner, ie for example by hot, cold, hot/cold or PIT emulsification. This involves a purely mechanical process in which no chemical reactions take place.

Finally, other known substances capable of absorbing radiation in the UV-A range may be additionally used provided they are stable in the overall system embracing the combination of UV-B and UV-A filters to be used in accordance with the present invention.

The present invention also relates to cosmetic and pharmaceutical formulations containing from 0.1 t o 10 wt, preferably from 1 to 7 wt, based on the total weight of the cosmetic and pharmaceutical formulation, of one or more compounds of formula I together with compounds acting as UV screening agents known to be suitable for cosmetic and pharmaceutical formulations, the compounds of formula I usually being used in smaller amounts than the UV-B-absorbing compounds.

The major portion of the screening agents in the cosmetic and pharmaceutical formulations serving to protect the human epidermis consists of compounds which absorb UV light in the UV-B range, ie radiation ranging from 280 to 320 nm. For example, the content of UV-A absorber used in accordance with the present invention is from 10 to 90 wt % and preferably from 20to 50 wt %, based on the total weight of UV-B and AV-A filter substances.

Suitable UV filter substances which can be used in combination with the compounds of formula I used in accordance with the invention are any desired UV-A and UV-B screening substances. Specific examples thereof are:

| No. | Substance | CAS No. (acid) |
| --- | --- | --- |
| 1 | 4-aminobenzoic acid | 150-13-0 |
| 2 | 3-(4-trimethylammonium)-benzylidenebornan-2-one methyl sulfate | 52793-97-2 |
| 3 | 3.3,5-trimethylcyclohexyl salicylate (homosalatum) | 118-56-9 |
| 4 | 2-hydroxy-4-methoxybenzophenone (oxybenzonum) | 131-57-7 |
| 5 | 2-phenylbenzimidazol-5-sulfonic acids and the potassium, sodium and triethanolamine salts thereof | 27503-81-7 |
| 6 | 3,3-(1,4-phenylenedimethine)-bis(7,7-dimethyl-2-oxobicyclo[2.2.1]heptane-1-methanesulfonic acid) and the salts thereof | 90457-82-2 |
| 7 | polyethoxyethyl 4-bis(polyethoxy)aminobenzoate | 113010-52-9 |
| 8 | 2-ethylhexyl 4-dimethylaminobenzoate | 21245-02-3 |
| 9 | 2-ethylhexyl salicylate | 118-60-5 |
| 10 | 2-isoamyl 4-methoxycinnamate | 7/6/7-10-2 |
| 11 | 2-ethylhexyl 4-methoxycinnamate | 5466-77-3 |
| 12 | 2-hydroxy-4-methoxybenzophenone-5-sulfone (sulisobenzonum) and the sodium salt | 4065-45-6 |
| 13 | 3-(4-sulfo)benzylidenebornan-2-one and salts | 58030-58-6 |
| 14 | 3-(4-methyl)benzylidenebornan-2-one | 36861-47-9 |
| 15 | 3-benzylidenebornan-2-one | 16087-24-8 |
| 16 | 1-(4-isopropylphenyl)-3-phenylpropane-1,3-dione | 63260-25-9 |
| 17 | 4-isopropylbenzyl salicylate | 94134-93-7 |
| 18 | 2,4,6-trianiline-(o-carbo-2'-ethylhexyl-1'-oxy)-1,3,5-triazine | 88122-99-0 |
| 19 | 3-imidazol-4-yl acrylic acid and the ethyl ester thereof | 104-98-3* |
| 20 | ethyl 2-cyano-3,3-diphenylacrylate | 5232-99-5 |
| 21 | 2-ethylhexyl 2-cyano-3,3-diphenylacrylate | 6197-30-4 |
| 22 | menthyl o-aminobenzoate or: 5-methyl-2-(1-methylethyl)-2-aminobenzoate | 134-09-8 |
| 23 | glyceryl p-aminobenzoate or: 1-glycerol 4-aminobenzoate | 136-44-7 |
| 24 | 2,2'-dihydroxy-4-methoxybenzophenone (dioxybenzone) | 131-53-3 |
| 25 | 2-hydroxy-4-methoxy-4-methylbenzophenone (mexonone) | 1641-17-4 |
| 26 | triethanolamine salicylate | 2174-16-5 |
| 27 | dimethoxyphenylglyoxalic acid or: sodium 3,4-dimethoxyphenylglyoxalate | |
| 28 | 3-(4'-sulfo)benzylidenebornan-2-one and its salts | 56039-58-8 |
| 29 | 4-tert-butyl-4'-methoxydibenzoylmethane | 70356-09-1 |
| 30 | 2,2',4,4'-tetrahydroxybenzophenone | 131-55-5 |

Finally, mikronized pigments such as titanium dioxide and zinc oxide may be mentioned.

For protection of human hair from UV radiation these screening agents of formula I of the invention may be incorporated in shampoos, lotions, gels or emulsions in concentrations of from 0.1 to 10 wt, preferably from 1 to 7 wt %. The respective formulations obtained may be used, inter alia, for washing, dyeing and styling the hair.

The compounds of the invention are usually distinguished by a particularly high absorbtive capacity in the range of UV-A radiation showing a well-defined band structure. Furthermore, they are readily soluble in cosmetic oils and are easy to corporate in cosmetic formulations. The emulsions formed using compounds I are particularly characterized by their high degree of stability, and the compounds I are themselves distinguished by high photostability, whilst the formulations prepared using compounds I are noted for their pleasant feeling on the skin.

The invention also relates to the compounds of the formula I for use as medicinal and pharmaceutical agents for prophylaxis of inflammation and allergies of the skin and also for the prevention of certain types of skin cancer, which agents contain an effective amount of at least one compound of formula I as active substance.

The pharmaceutical agents of the invention can be administered orally or topically. For oral administration, the pharmaceutical agents exist in the form of, inter alia, pastilles, gelatine capsules, dragees, syrups, solutions, emulsions or suspensions. Topical administration of the pharmaceutical agents is effected, for example, by applying them in an ointment, cream, gel, spray, solution or lotion.

EXAMPLES

I. Preparation

Example 1

General specification (for compound No. 1 in Table 2)

0.1 mol of 2-ethylhexyl p-aminobenzoate, 0.1 mol of pivaloyl acetonitrile and 0.1 mol of triethyl orthoformate were heated in 100 mL of diethylene glycol for 2 h at 120° C., ethanol being removed by distillation. After cooling to 80 ° C. water was added and the precipitate was removed by filtration. The mother liquor was then recrystallized from petroleum ether. There was obtained compound 1 in Table 2 in a yield of 80%.

EXAMPLE 2

0.1 mol of 2-ethylhexyl anthranilate, 0.1 mol of 2,4-pentanedione and 0.1 mol of triethyl orthoformate were heated in 100 mL of diethylene glycol for 2 h at 120° C., ethanol being removed by distillation. After cooling to 80 ° C. water was added and the precipitate was removed by filtration. The mother liquor was then recrystallized from petroleum ether. There was obtained compound 24 in Table 2 in a yield of 70%.

EXAMPLE 3

0.1 mol of m-toluidine, 0.1 mol of pivaloyl acetonitrile and 0.1 mol of triethyl orthoformate and 1 g of zinc chloride were heated in 100 mL of diethylene glycol for 2 h at 120° C., ethanol being removed by distillation. After cooling to 80° C. water was added and the precipitate was removed by filtration. The mother liquor was then recrystallized from petroleum ether. There was obtained compound 2 in Table 2 in a yield of 70%.

Other compounds thus prepared are listed in the following Table 2.

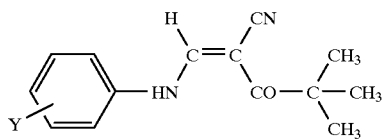

| No. | Y | $\lambda_{max}$ | E'1 |
|---|---|---|---|
| 1) | 4-COOC$_8$H$_{17}$[1] | 346 | 860 |
| 2) | 3-CH$_3$ | 338 | 978 |
| 3) | 4-OCH$_3$ | 348 | 841 |
| 4) | 4-tert-C$_4$H$_9$ | 342 | 888 |
| 5) | 4-n-C$_4$H$_9$ | 342 | 884 |
| 6) | 4-CONHC$_8$H$_{17}$[1] | 346 | 773 |
| 7) | 4-iso-C$_3$H$_7$ | 342 | 903 |
| 8) | 4-n-C$_3$H$_7$ | 342 | 918 |
| 9) | 2-COOC$_8$H$_{17}$[1] | 348 | 717 |
| 10) | 2-CN | 338 | 995 |
| 11) | 2-COOC$_{15}$H$_{31}$(iso)$^{(oil)}$ | 346 | 583 |
| 12) | 3-iso-OC$_3$H$_7$ | 340 | 829 |
| 13) | 2-COO$^{\ominus}$ × N$^{\oplus}$H(C$_2$H$_4$OH)$_3$ | 346 | 667 (water) |
| 14) | 2,5-di-OCH$_3$ | 362 | 491 |
| 15) | 2-COOH | 346 | 965 |
| 16) | 4-SO$_3^{\ominus}$ × $^{\oplus}$HN(C$_2$H$_4$OH)$_3$ | 340 | 666 (water) |
| 17) | 4-SO$_3^{\ominus}$ Na$^{\oplus}$ | 340 | 1010 (water) |
| 18) | 2-OC$_2$H$_5$ | 352 | 876 |
| 19) | 2-COOCH$_3$ | 348 | 995 |
| 20) | 2-COOCH$_2$CH(CH$_3$)$_2$ | 348 | 864 |
| 21) | 2-COOC$_4$H$_9$ | 346 | 825 |
| 22) | (structure shown) | 380 | 768 |

General manufacturing instructions for the preparation of emulsions for cosmetic purposes All oil-soluble components are heated in a stirred boiler at 85° C. When all of the components have melted or exist as liquid phase, the aqueous phase is incorporated whilst effecting homogenization. Stirring is continued while the emulsion is cooled to approximately 40° C., scented, homogenized and then cooled to 25° C. with constant stirring.
Formulations Example 4

Composition for lip care

Mass content in wt %

| | |
|---|---|
| ad 100 | eucerinum anhydricum |
| 10.00 | glycerol |
| 10.00 | titanium dioxide |
| 5.00 | compound No. 1 of Table 2 |
| 8.00 | octyl methoxycinnamate |
| 5.00 | zinc oxide |
| 4.00 | castor oil |
| 4.00 | pentaerythritol stearate/caprate/caprylate adipate |
| 3.00 | glyceryl stearate SE |
| 2.00 | beeswax |
| 2.00 | microcrystalline wax |
| 2.00 | quaternium-18 bentonite |
| 1.50 | poly(PEG-45-co-dodecyl glycol) |

Example 5

Composition for lip care

Mass content in wt %

| | |
|---|---|
| ad 100 | eucerinum anhydricum |
| 10.00 | glycerol |
| 10.00 | titanium dioxide |
| 5.00 | compound No. 24 of Table 2 |
| 8.00 | octyl methoxycinnamate |
| 5.00 | zinc oxide |
| 4.00 | castor oil |
| 4.00 | pentaerythritol stearate/caprate/caprylate adipate |
| 3.00 | glyceryl stearate SE |
| 2.00 | beeswax |
| 2.00 | microcrystalline wax |
| 2.00 | quaternium-18 bentonite |
| 1.50 | poly(PEG-45-co-dodecyl glycol) |

Example 6

Composition for sun blockers containing micropigments

Mass content in wt %

| | |
|---|---|
| ad 100 | water |
| 10.00 | octyl methoxycinnamate |
| 6.00 | PEG-7-hyrogenated castor oil |
| 6.00 | titanium dioxide |
| 5.00 | compound No. 1 of Table 2 |
| 5.00 | mineral oil |
| 5.00 | isoamyl p-methoxycinnamate |
| 5.00 | propylene glycol |
| 3.00 | jojoba oil |
| 3.00 | 4-methylbenzylidene campher |
| 2.00 | poly(PEG-45-co-dodecyl glycol) |
| 1.00 | dimethicone |
| 0.50 | PEG-40-hydrogenated castor oil |
| 0.50 | tocopheryl acetate |
| 0.50 | phenoxyethanol |
| 0.20 | EDTA |

Example 7

Mass content in wt %

| | |
|---|---|
| ad 100 | water |
| 10.00 | octyl methoxycinnamate |
| 6.00 | PEG-7-hyrogenated castor oil |
| 6.00 | titanium dioxide |
| 5.00 | compound No. 24 of Table 2 |
| 5.00 | mineral oil |
| 5.00 | isoamyl p-methoxycinnamate |
| 5.00 | propylene glycol |
| 3.00 | jojoba oil |
| 3.00 | 4-methylbenzylidene campher |
| 2.00 | poly(PEG-45-co-dodecyl glycol) |
| 1.00 | dimethicone |
| 0.50 | PEG-40-hydrogenated castor oil |
| 0.50 | tocopheryl acetate |
| 0.50 | phenoxyethanol |
| 0.20 | EDTA |

Example 8

Grease-free gel

| Mass content in wt % | |
|---|---|
| ad 100 | water |
| 8.00 | octyl methoxycinnamate |
| 7.00 | titanium dioxide |
| 5.00 | compound No. 1 of Table 2 |
| 5.00 | glycerol |
| 5.00 | PEG-2 PABA |
| 1.00 | 4-methylbenzylidene campher |
| 0.40 | poly(acrylate-cross-$C_{10}$–$C_{30}$ alkyl acrylate) |
| 0.30 | imidazolidinyl urea |
| 0.25 | hydroxyethyl cellulose |
| 0.25 | sodium methylparaben |
| 0.20 | disodium EDTA |
| 0.15 | fragrance |
| 0.15 | sodium propylparaben |
| 0.10 | sodium hydroxide |

Example 9

Grease-free gel

| Mass content in wt % | |
|---|---|
| ad 100 | water |
| 8.00 | octyl methoxycinnamate |
| 7.00 | titanium dioxide |
| 5.00 | compound No. 24 of Table 2 |
| 5.00 | glycerol |
| 5.00 | PEG-2 PABA |
| 1.00 | 4-methylbenzylidene campher |
| 0.40 | poly(acrylate-cross-$C_{10}$–$C_{30}$ alkyl acrylate) |
| 0.30 | imidazolidinyl urea |
| 0.25 | hydroxyethyl cellulose |
| 0.25 | sodium methylparaben |
| 0.20 | disodium EDTA |
| 0.15 | fragrance |
| 0.15 | sodium propylparaben |
| 0.10 | sodium hydroxide |

Example 10

Sun-shading cream (LSF 20)

| Mass content in wt % | |
|---|---|
| ad 100 | water |
| 8.00 | octyl methoxycinnamate |
| 8.00 | titanium dioxide |
| 6.00 | PEG-7-hyrogenated castor oil |
| 5.00 | compound No. 1 of Table 2 |
| 6.00 | mineral oil |
| 5.00 | zinc oxide |
| 5.00 | isopropyl palmitate |
| 5.00 | imidazolidinyl urea |
| 3.00 | jojoba oil |
| 2.00 | poly(PEG-45-co-dodecyl glycol) |
| 1.00 | 4-methylbenzylidene campher |
| 0.60 | magnesium stearate |
| 0.50 | tocopheryl acetate |
| 0.25 | methylparaben |
| 0.20 | disodium EDTA |
| 0.15 | propylparaben |

Example 11

Sun-shading cream (LSF 20)

| Mass content in wt % | |
|---|---|
| ad 100 | water |
| 8.00 | octyl methoxycinnamate |
| 8.00 | titanium dioxide |
| 6.00 | PEG-7-hyrogenated castor oil |
| 5.00 | compound No. 24 of Table 2 |
| 6.00 | mineral oil |
| 5.00 | zinc oxide |
| 5.00 | isopropyl palmitate |
| 5.00 | imidazolidinyl urea |
| 3.00 | jojoba oil |
| 2.00 | poly(PEG-45-co-dodecyl glycol) |
| 1.00 | 4-methylbenzylidene campher |
| 0.60 | magnesium stearate |
| 0.50 | tocopheryl acetate |
| 0.25 | methylparaben |
| 0.20 | disodium EDTA |
| 0.15 | propylparaben |

Example 12

Sun-shading cream, waterproof

| Mass content in wt % | |
|---|---|
| ad 100 | water |
| 8.00 | octyl methoxycinnamate |
| 5.00 | PEG-7-hyrogenated castor oil |
| 5.00 | propylene glycol |
| 4.00 | isopropyl palmitate |
| 4.00 | caprylic/capric triglyceride |
| 5.00 | compound No. 1 of Table 2 |
| 4.00 | glycerol |
| 3.00 | jojoba oil |
| 1.00 | 4-methylbenzylidene campher |
| 2.00 | titanium dioxide |
| 1.50 | poly(PEG-45-co-dodecyl glycol) |
| 1.50 | dimethicone |
| 0.70 | magnesium sulfate |
| 0.50 | magnesium stearate |
| 0.15 | fragrance |

Example 13

Sun-shading cream, waterproof

| Mass content in wt % | |
|---|---|
| ad 100 | water |
| 8.00 | octyl methoxycinnamate |
| 5.00 | PEG-7-hyrogenated castor oil |
| 5.00 | propylene glycol |
| 4.00 | isopropyl palmitate |
| 4.00 | caprylic/capric triglyceride |
| 5.00 | compound No. 24 of Table 2 |
| 4.00 | glycerol |
| 3.00 | jojoba oil |
| 2.00 | 4-methylbenzylidene campher |
| 2.00 | titanium dioxide |
| 1.50 | poly(PEG-45-co-dodecyl glycol) |
| 1.50 | dimethicone |
| 0.70 | magnesium sulfate |
| 0.50 | magnesium stearate |
| 0.15 | fragrance |

Example 14

Sun-shading lotion (LSF 6)

| Mass content in wt % | |
|---|---|
| ad 100 | water |
| 10.00 | mineral oil |
| 6.00 | PEG-7-hyrogenated castor oil |
| 5.00 | isopropyl palmitate |
| 4.00 | caprylic/capric triglyceride |
| 3.50 | octyl methoxycinnamate |
| 5.00 | compound No. 1 of Table 2 |
| 3.00 | caprylic/capric triglyceride |
| 3.00 | jojoba oil |
| 2.00 | poly(PEG-45-co-dodecyl glycol) |
| 0.70 | magnesium sulfate |
| 0.60 | magnesium stearate |
| 0.50 | tocopheryl acetate |
| 0.30 | glycerol |
| 0.25 | methylparaben |
| 0.15 | polyparaben |
| 0.05 | tocopherol |

Example 15

Sun-shading lotion (LSF 6)

| Mass content in wt % | |
|---|---|
| ad 100 | water |
| 10.00 | mineral oil |
| 6.00 | PEG-7-hyrogenated castor oil |
| 5.00 | isopropyl palmitate |
| 4.00 | caprylic/capric triglyceride |
| 3.50 | octyl methoxycinnamate |
| 5.00 | compound No. 24 of Table 2 |
| 3.00 | caprylic/capric triglyceride |
| 3.00 | jojoba oil |
| 2.00 | poly(PEG-45-co-dodecyl glycol) |
| 0.70 | magnesium sulfate |
| 0.60 | magnesium stearate |
| 0.50 | tocopheryl acetate |
| 0.30 | glycerol |
| 0.25 | methylparaben |
| 0.15 | polyparaben |
| 0.05 | tocopherol |

Example 16

Sun-shading cream, waterproof

| Mass content in wt % | |
|---|---|
| ad 100 | water |
| 8.00 | octyl methoxycinnamate |
| 5.00 | PEG-7-hyrogenated castor oil |
| 5.00 | propylene glycol |
| 4.00 | isopropyl palmitate |
| 4.00 | caprylic/capric triglyceride |
| 3.00 | compound No. 17 of Table 2 |
| 2.00 | compound No. 24 of Table 2 |
| 4.00 | glycerol |
| 3.00 | jojoba oil |
| 2.00 | 4-methylbenzylidene campher |

Sun-shading cream, waterproof (continued)

| Mass content in wt % | |
|---|---|
| 2.00 | titanium dioxide |
| 1.50 | poly(PEG-45-co-dodecyl glycol) |
| 1.50 | dimethicone |
| 0.70 | magnesium sulfate |
| 0.50 | magnesium stearate |
| 0.15 | fragrance |

Example 17

Sun-shading lotion (LSF 6)

| Mass content in wt % | |
|---|---|
| ad 100 | water |
| 10.00 | mineral oil |
| 6.00 | PEG-7-hyrogenated castor oil |
| 5.00 | isopropyl palmitate |
| 3.50 | octyl methoxycinnamate |
| 5.00 | compound No. 24 of Table 2 |
| 3.00 | caprylic/capric triglyceride |
| 3.00 | jojoba oil |
| 2.00 | poly(PEG-45-co-dodecyl glycol) |
| 0.70 | magnesium sulfate |
| 0.60 | magnesium stearate |
| 0.50 | tocopheryl acetate |
| 0.30 | glycerol |
| 0.25 | methylparaben |
| 0.15 | polyparaben |
| 0.05 | tocopherol |

We claim:

1. A method of using a compound of formula I

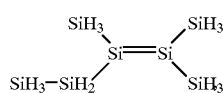

(I)

in which the C=C double bond is present in E and/or Z configuration and the variables have the following meanings:

$R^1$ denotes $COOR^5$, $COR^5$, $CONR^5R^6$, $CN$, $O=S(-R^5)=O$, $O=S(-OR^5)=O$, $R^7O-P(-OR^8)=O$;

$R^2$ denotes $COOR^6$, $COR^6$, $CONR^5R^6$, $CN$, $O=S(-R^6)=O$, $O=S(-OR^6)=O$, $R^7O-P(-OR^8)=O$;

$R^3$ denotes hydrogen, an optionally substituted aliphatic, cycloaliphatic, araliphatic or aromatic radical having in each case up to 18 carbon atoms;

$R^4$ denotes an optionally substituted aromatic or heteroaromatic radical containing from 5 to 12 ring atoms;

$R^5$ to $R^8$ independently denote hydrogen, an open-chain or branched-chain aliphatic, araliphatic, cycloaliphatic or optionally substituted aromatic radical containing in each case up to 18 carbon atoms, where the variables $R^3$ to $R^8$ may also form, together with the carbon atoms to which they are attached, a 5-membered or 6-membered ring, which may be anellated if desired, as UV filters, particularly UV-A filters, in cosmetic and pharmaceutical formulations for the protection of the human skin or human hair from solar radiation, alone or together with compounds known per se in cosmetic and pharmaceutical formulations and capable of absorbing radiation in the UV range.

2. A method of using a compound of formula I as defined in claim 1 as a UV-A filter.

3. A method of using a compound of formula I as defined in claim 1, in which formula $R^3$ stands for hydrogen, $R^1$ stands for CN, $COOR^5$ and $COR^5$ and $R^2$ stands for CN, $COOR^6$ and $COR^6$, where $R^5$ and $R^6$ independently denote open-chain or branched-chain aliphatic or optionally substituted aromatic radicals containing up to 8 carbon atoms.

4. A method of using a compound of formula I as defined in claim 1, in which formula $R^4$ stands for phenyl optionally substituted by hydrophilic or lipophilic substituents.

5. A method of using a compound of formula I as defined in claim 1, in which formula $R^4$ stands for an alkoxyphenyl or alkoxycarbonylphenyl radical.

6. A method of using a compound of formula I as defined in claim 1, in which formula $R^4$ stands for a phenyl radical carrying water-soluble substituents selected from the group consisting of carboxylate, sulfonate or ammonium radicals.

7. A cosmetic or pharmaceutical formulation for the protection of the human epidermis or human hair from UV light ranging from 280 to 400 nm and containing a screening agent, wherein said formulation contains, as photo-stable UV filter, in a cosmetic or pharmaceutical carrier, alone or together with a compound capable of absorbing UV radiation and known to be suitable for cosmetic and pharmaceutical formulations, an effective amount of a compound of formula I

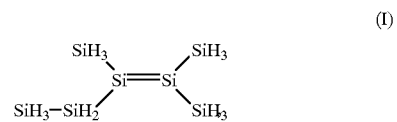
(I)

in which the variables have the meanings defined in claim 1.

8. A screening agent as defined in claim 7, containing as UV-A filter a compound of formula I, in which $R^3$ stands for hydrogen, $R^1$ stands for CN, $COOR^5$ and $COR^5$ and $R^2$ stands for CN, $COOR^6$ or $COR^6$, where $R^5$ and $R^6$ denote optionally substituted aliphatic or aromatic radicals containing up to 8 carbon atoms.

9. A screening agent as defined in claim 7, containing as UV-A filter a compound of formula I, in which $R^4$ stands for phenyl optionally substituted by hydrophilic or lipophilic substituents.

10. A screening agent as defined in claim 7, containing as UV-A filter a compound of formula I, in which $R^3$ stands for hydrogen, $R^1$ stands for CN, $COOR^5$ or $COR^5$ and $R^2$ stands for CN, $COOR^6$ or $COR^6$ and $R^4$ stands for a phenyl radical which may be substituted by alkyl, alkoxy, alkylaminocarbonyl, alkoxycarbonyl radicals, containing in each case up to 20 carbon atoms, or containing cyanogen or carboxy radicals, and also containing water-solubilizing substituents selected from the group consisting of carboxylate, sulfonate or ammonium radicals.

11. A pharmaceutical formulation, containing an effective amount of at least one compound of formula I as defined in claim 1.

* * * * *

UNITED STATES PATENT AND TRADEMARK OFFICE
CERTIFICATE OF CORRECTION

PATENT NO.: 5,945,091

DATED: August 31, 1999

INVENTOR(S): HABECK et al.

It is certified that error appears in the above-identified patent and that said Letters Patent is hereby corrected as shown below:

Col. 36, claim 1, line 40, and col. 38, claim 7, line 5, delete the formula (I) shown and substitute the following formula (I):

Signed and Sealed this

First Day of February, 2000

Attest:

Attesting Officer

Q. TODD DICKINSON

Acting Commissioner of Patents and Trademarks

UNITED STATES PATENT AND TRADEMARK OFFICE
CERTIFICATE OF CORRECTION

PATENT NO.: 5,945,091

DATED: August 31, 1999

INVENTOR(S): HABECK et al.

It is certified that error appears in the above-identified patent and that said Letters Patent is hereby corrected as shown below:

Col. 31, line 38, insert the following missing compounds from Table 2:

| | | | |
|---|---|---|---|
| 23) | [structure] | 350 | 817 |
| 24) | [structure] | 344 | 795 |
| 25) | [structure] | 344 | 938 |
| 26) | [structure] | 336 | 1035 |
| 27) | [structure] | 346 | 1049 |

UNITED STATES PATENT AND TRADEMARK OFFICE
CERTIFICATE OF CORRECTION

PATENT NO.: 5,945,091

DATED: August 31, 1999

INVENTOR(S): HABECK et al.

It is certified that error appears in the above-identified patent and that said Letters Patent is hereby corrected as shown below:

| 28) | [structure with HN-phenyl-COOC$_8$H$_{17}$ [1], C=C, COCH$_3$, COOC$_2$H$_5$] | 346 | 757 |
|---|---|---|---|
| 29) | [structure with HN-phenyl-COOC$_8$H$_{17}$ [1] (para), C=C, COCH$_3$, COOCH$_3$] | 346 | 941 |
| 30) | [structure with HN-phenyl-COOCH$_3$, C=C, COCH$_3$, COOCH$_3$] | 344 | 1008 |
| 31) | [structure with HN-phenyl-COOC$_8$H$_{17}$ [1], C=C, COCH$_3$, COOC(CH$_3$)$_3$] | 344 | 717 |
| 32) | [structure with HN-phenyl-OCH$_3$-OCH$_3$, C=C, CN, COOC$_8$H$_{17}$ [1]] | 346 | 646 |

UNITED STATES PATENT AND TRADEMARK OFFICE
CERTIFICATE OF CORRECTION

PATENT NO.: 5,945,091

DATED: August 31, 1999

INVENTOR(S): HABECK et al.

It is certified that error appears in the above-identified patent and that said Letters Patent is hereby corrected as shown below:

| 33) | [structure: H–C=C(CN)(COOC$_8$H$_{17}$) with HN-aryl bearing OCH$_3$ and H$_3$CO substituents] [1] | 350 | 612 |
|---|---|---|---|
| 34) | [structure: H–C=C(CN)(COOC$_8$H$_{17}$) with HN-aryl bearing two OCH$_3$ groups (3,5-dimethoxy)] [1] | 322 | 761 |
| 35) | [structure: H–C=C(CN)(COOC$_8$H$_{17}$) with HN-aryl bearing COOC$_2$H$_5$] [1] | 332 | 1105 |
| 36) | [structure: H–C=C(CN)(COOC$_8$H$_{17}$) with HN-aryl bearing COOCH$_3$] [1] | 336 | 752 |
| 37) | [structure: H–C=C(COOC$_2$H$_5$)(COOC$_2$H$_5$) with HN-aryl bearing COOCH$_3$] | 336 | 890 |

UNITED STATES PATENT AND TRADEMARK OFFICE
CERTIFICATE OF CORRECTION

PATENT NO.: 5,945,091

DATED: August 31, 1999

INVENTOR(S): HABECK et al.

It is certified that error appears in the above-identified patent and that said Letters Patent is hereby corrected as shown below:

| | | | |
|---|---|---|---|
| 38) | 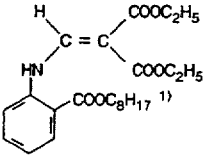 | 335 | 630 |
| 39) | 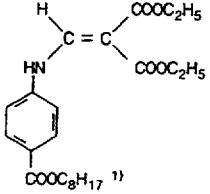 | 320 | 700 |
| 40) | 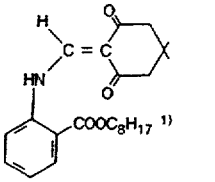 | 358 | 743 |
| 41) | 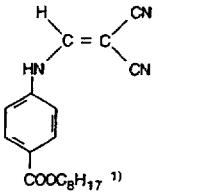 | 330 | 1191 |
| 42) | 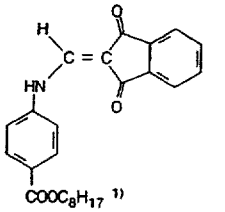 | 374 | 1175 |

UNITED STATES PATENT AND TRADEMARK OFFICE
CERTIFICATE OF CORRECTION

PATENT NO.: 5,945,091

DATED: August 31, 1999

INVENTOR(S): HABECK et al.

It is certified that error appears in the above-identified patent and that said Letters Patent is hereby corrected as shown below:

| 43) | [structure: H-C=C(CN)(COPh) with HN-C6H4-COOC8H17 [1)]] | 362 | 869 |
|---|---|---|---|
| 44) | [structure: H-C=C(cyclic Meldrum-type) with HN-C6H4-COOC8H17 [1)]] | 336 | 896 |

[1)] $C_8H_{17}$ = 2-ethylhexyl --

Signed and Sealed this

Twenty-fifth Day of April, 2000

Attest:

Q. TODD DICKINSON

*Attesting Officer*   *Director of Patents and Trademarks*